(12) United States Patent
Katayose et al.

(10) Patent No.: US 6,495,270 B1
(45) Date of Patent: Dec. 17, 2002

(54) COMPOUNDS, HARDENING ACCELERATOR, RESIN COMPOSITION, AND ELECTRONIC PART DEVICE

(75) Inventors: Mitsuo Katayose; Shinya Nakamura, both of Ibaraki (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 0 days.

(21) Appl. No.: 09/622,569

(22) PCT Filed: Feb. 18, 1999

(86) PCT No.: PCT/JP99/00710

§ 371 (c)(1),
(2), (4) Date: Oct. 23, 2000

(87) PCT Pub. No.: WO99/42449

PCT Pub. Date: Aug. 26, 1999

(30) Foreign Application Priority Data

Feb. 19, 1998 (JP) ............................................ 10-037234

(51) Int. Cl.⁷ .............................................. H01L 29/12
(52) U.S. Cl. ................ 428/620; 523/466; 525/523; 528/94; 528/111; 528/116; 528/117; 528/118; 528/119; 548/354.1
(58) Field of Search ................................ 523/440–444, 523/458, 460, 466; 525/523; 528/94, 111, 116, 117, 118, 119; 548/354.1; 257/787, 793, 795, 796; 428/620

(56) References Cited

FOREIGN PATENT DOCUMENTS

| JP | 55-5929 | 1/1980 |
|---|---|---|
| JP | 56-94761 | 7/1981 |
| JP | 56-131620 | 10/1981 |
| JP | 57-210647 | 12/1982 |
| JP | 58-57427 | 4/1983 |
| JP | 59-8721 | 1/1984 |
| JP | 59-8722 | 1/1984 |
| JP | 59-75923 | 4/1984 |
| JP | 59-136321 | 8/1984 |
| JP | 61-151231 | 7/1986 |
| JP | 62-16484 | 1/1987 |
| JP | 62-81416 | 4/1987 |
| JP | 62-246925 | 10/1987 |
| JP | 63-12627 | 1/1988 |
| JP | 63-20325 | 1/1988 |
| JP | 63-146919 | 6/1988 |
| JP | 63-210121 | 8/1988 |
| JP | 64-38416 | 2/1989 |
| JP | 64-65116 | 3/1989 |
| JP | 1-105562 | 4/1989 |
| JP | 1-236263 | 9/1989 |
| JP | 1-236264 | 9/1989 |
| JP | 2-34627 | 2/1990 |
| JP | 2-189330 | 7/1990 |
| JP | 2-189331 | 7/1990 |
| JP | 2-240130 | 9/1990 |
| JP | 2-240131 | 9/1990 |
| JP | 3-9919 | 1/1991 |
| JP | 3-16243 | 1/1991 |
| JP | 3-26901 | 2/1991 |
| JP | 3-67243 | 3/1991 |
| JP | 3-116958 | 5/1991 |
| JP | 4-65420 | 3/1992 |
| JP | 4-85321 | 3/1992 |
| JP | 4-91121 | 3/1992 |
| JP | 4-96922 | 3/1992 |
| JP | 4-96930 | 3/1992 |
| JP | 5-9268 | 1/1993 |
| JP | 5-198940 | 8/1993 |
| JP | 6-228414 | 8/1994 |
| JP | 7-188395 | 7/1995 |
| JP | 7-228664 | 8/1995 |
| JP | 7-330868 | 12/1995 |
| JP | 8-3280 | 1/1996 |
| JP | 8-92355 | 4/1996 |
| JP | 8-92356 | 4/1996 |
| JP | 8-109246 | 4/1996 |
| JP | 8-157564 | 6/1996 |
| JP | 8-157565 | 6/1996 |
| JP | 9-157497 | 6/1997 |
| JP | 10-237161 | 9/1998 |
| JP | 10-259236 | 9/1998 |

OTHER PUBLICATIONS

Morrison & Boyd, *Organic Chemistry*, Allyn & Bacon, Inc. p. 358, 1966.*
Encyclopedia of Polymer Science & Technology, John Wiley and Sons, p. 230, 1967.*
*Tetrahedron*, Escolastico et al., Pergamon, vol. 50, No. 43, pp. 12489 & 12490, 1994.*
Lee & Neville, *Handbook of Epoxy Resins*, McGraw–Hill pp. 11–13 to 11–14, 1967.*
Escolasico, C et al Imidazole and Bensiidazole Addition to Quinones. Formation of meso and d,l Isomers and Crystal Structure of the d,I isomers of 2,3–Bis(beximidazol–1'–yl)–1,4–dihyroxybenzene. Tetrahedron, 50(43), 12489–510 (1994).

* cited by examiner

*Primary Examiner*—Robert Dawson
*Assistant Examiner*—D. Aylward
(74) *Attorney, Agent, or Firm*—Antonelli, Terry, Stout & Kraus, LLP

(57) ABSTRACT

Nitrogen compounds represented by formula (XXIa) or (XXIb); an epoxy resin hardening accelerator and a resin composition each containing any of the compounds; and an electronic part device containing an element encapsulated with the composition. In the formulae, $R^1$ and $R^2$ each represents hydrogen or a $C_{1-20}$ monovalent organic group; $R^3$ and $R^4$ each represents a $C_{1-20}$ divalnt organic group; $R^5$ represents hydrogen or a $C_{1-6}$ monovalent organic group; k is an integer of 0 to 2; and p is 0 or 1.

24 Claims, 10 Drawing Sheets

COMPOUNDS, HARDENING ACCELERATOR, RESIN COMPOSITION, AND ELECTRONIC PART DEVICE

TECHNICAL FIELD

This invention relates to a novel compound, a resin composition suited as molding materials, insulating-layer materials and adhesive materials, a curing accelerator for the resin composition, and an electronic component device obtained by encapsulating device components with the resin composition.

BACKGROUND ART

Epoxy resin is conventionally used in a wide range as molding materials, insulating-layer materials and adhesive materials, and epoxy resin compositions are in wide use in the field of the encapsulation of device components in electronic component parts such as transistors and ICs (integrated circuits). This is because the epoxy resin has properties such as molding properties, electrical properties, moisture resistance, heat resistance, mechanical properties and adhesion to component inserts which are well balanced.

As curing accelerators for epoxy resin, Japanese Patent Application Laid-open KOKAI No. 55-5929, No. 56-94761, No. 56-131620, No. 58-57427, No. 57-210647, No. 59-136321, No. 61-151231, No. 63-12627, No. 63-20325, No. 63-210121, No. 1-105562, No. 1-236263, No. 1-236264, No. 2-34627, No. 5-9268, No. 5-198940, No. 6-228414, No. 7-228664, No. 7-188395, No. 8-3280, No. 7-330868, No. 8-92355, No. 8-92356, No. 8-157565 and No. 8-157564 disclose 1,8-diazabicyclo[5.4.0]undecene-7, or its phenolic salt, phenolic resin salt, aromatic carboxylate, aromatic sulfonate, fatty acid salt or carbonate. Japanese Patent Application Laid-open KOKAI No. 3-116958 discloses silicon derivatives of 1,8-diazabicyclo[5.4.0]undecene-7. Use of these curing accelerators, however, has involved a problem that the epoxy resin is affected by humidity in service environment and may have a low curing performance depending on moisture absorption to cause various faulty molding such as faulty mold release, runner break and gate break.

Japanese Patent Applications Laid-open KOKAI No. 62-81416, No. 1-65116 and No. 3-9919 also disclose methods of use of 1,8-diazabicyclo[5.4.0]undecene-7 or a salt thereof in the form of its mixture with a triorganophosphine. Japanese Patent Applications Laid-open KOKAI No. 62-16484, No. 1-38416, No. 2-189331, No. 2-240131, No. 4-65420, No. 4-85321, No. 4-91121, No. 4-96922, No. 4-96930 and No. 8-109246 disclose methods of use of 6-dialkylamino-1,8-diazabicyclo[5.4.0]undecene-7 or salts thereof. Japanese Patent Applications Laid-open KOKAI No. 59-8721, No. 59-8722 and No. 3-16243 disclose methods of use of 1,5-diazabicyclo[4.3.0]nonene-5, and also Japanese Patent Applications Laid-open KOKAI No. 63-146919, No. 2-189330 and No. 2-240130 disclose methods of use of a guanidine compound. These methods promise a superiority in rapid curability and curability under moisture absorption but, on the other hand, have involved a problem that a difficulty in molding as exemplified by faulty filling may occur because of a short pot life, an increase in melt viscosity and a decrease in flow properties or that the performance of molded products may lower, e.g., gold wires of IC chips break to cause faulty conduction. Accordingly, under existing circumstances, epoxy resin compositions which employ such a technique and molding materials for encapsulation which make use of such resin compositions must be stored and transported under refrigeration, and require a high cost.

Japanese Patent Applications Laid-open KOKAI No. 59-75923, No. 62-246925 and No. 3-26901 disclose that tetraphenyl borate of 1,8-diazabicyclo[5.4.0]undecene-7 is effective for the improvement of pot life. This tetraphenyl borate has so strong an ionic bond and so high a melting point as to have a low dispersibility, bringing about a good pot life. It, however, can not exhibit any good curability.

In addition, in recent years, as the greatest problem in molding materials for encapsulating semiconductors such as ICs and LSIs (large-scale integrated circuits), there is a problem of what is called solder reflow cracking, which is cracking caused when packages are assembled. In order to improve reflow cracking resistance, resin compositions are proposed which contain an inorganic filler in a large quantity. The inorganic filler, however, must be mixed in a quantity limited because its use in a large quantity causes a lowering of flow properties at the time of molding. Hence, this technique can not be expected to bring about any remarkable improvement in reflow cracking resistance. Accordingly, as a way of overcoming such a problem, it is proposed in Japanese Patent Application Laid-open KOKAI No. 9-157497 that an addition product of triphenylphosphine with 1,4-benzoquinone is used as a curing accelerator, which, however, has involved the problem of a short pot life.

As discussed above in detail, any conventional curing accelerators can not satisfy all the rapid curability, curability after moisture absorption under moist condition, pot life and flow properties of epoxy resin compositions.

DISCLOSURE OF THE INVENTION

The present invention was made taking account of the problems discussed above. An object of the present invention is to provide an epoxy resin composition having all the rapid curability, curability after moisture absorption under moist condition, pot life and flow properties in a good state, a curing accelerator used therefor, an electronic component device having device components encapsulated with such a composition, and a novel compound suited as the curing accelerator.

The present inventors have discovered that the rapid curability, curability after moisture absorption under moist condition, pot life and flow properties of epoxy resin compositions can be improved by mixing a nitrogen-containing compound obtained by the addition of a specific amidine compound with a specific quinone compound, thus they have accomplished the present invention.

To achieve the above object, the present invention provides a nitrogen-containing compound which is an addition product of an amidine compound represented by the following Formula (XXa) or (XXb) with a quinone compound represented by the following Formula (II).

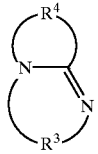

(XXa)

-continued

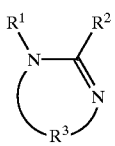

(XXb)

In Formula (XXa) or (XXb), $R^1$ and $R^2$ each represent a hydrogen atom, an amino group or a monovalent organic group having 1 to 20 carbon atoms. The organic group may preferably have 2 to 15 carbon atoms, and more preferably 2 to 10 carbon atoms. $R^3$ and $R^4$ each represent a divalent organic group having 1 to 20 carbon atoms, which may preferably have 2 to 15 carbon atoms, and more preferably 2 to 10 carbon atoms.

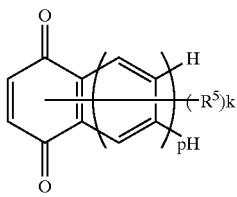

(II)

In Formula (II), $R^5$ represents a hydrogen atom or a monovalent organic group having 1 to 6 carbon atoms, and k and p represent an integer of 0 to 2 and an integer of 0 or 1, respectively.

$R^1$ and $R^2$ may each preferably be selected from a hydrogen atom and substituted or unsubstituted alkyl, aryl, aralkyl, alkenyl and alkoxyl groups. $R^3$ and $R^4$ form part of the ring structure, and may preferably be selected from a substituted or unsubstituted, saturated or unsaturated hydrocarbon group, and a saturated or unsaturated hydrocarbon group containing a carbonyl linkage, an imino linkage or an ether linkage. $R^5$ may preferably be selected from a hydrogen atom and an alkyl group, an alkoxyl group, an aryl group and an aralkyl group which have 1 to 6 carbon atoms.

As stated above, the groups represented by $R^1$ to $R^4$ may be those in which a substituent is further bonded to the basic structure of alkyl group, aryl group, aralkyl group, alkenyl group or alkoxyl group. As examples of such a substituent, it may include alkyl groups such as a methyl group and an ethyl group, aryl groups such as a phenyl group and a naphthyl group, alkoxyl groups such as a methoxyl group, an ethoxyl group and butoxy group, a hydroxyl group, hydroxyaryl groups, an amino group, alkylamino groups, cyanoalkyl groups and alkylaryl groups.

The above amidine compound may preferably be a compound represented by the following Formula (I).

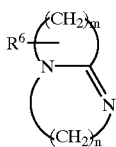

(I)

wherein $R^6$ is selected from a hydrogen atom and an alkyl group, a dialkylamino group, an aryl group and an aralkyl group which have 1 to 12 carbon atoms; and m and n represent integers of 2 to 5 which are independent from each other.

Of the compounds represented by Formula (I), 1,8-diazabicyclo[5.4.0]undecene-7 and 1,5-diazabicyclo[4.3.0] nonene-5 are particularly preferred, and these may be used alone or in combination. As the quinone compound represented by the above Formula (II), 1,4-benzoquinone and 2,5-toluquinone are preferred, and these may be used alone or in combination.

The present invention also provides a nitrogen-containing compound represented by the following Formula (XXIa) or (XXIb)

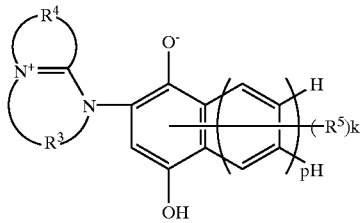

(XXIa)

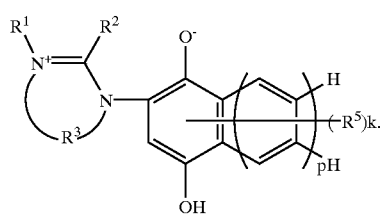

(XXIb)

In the above Formula (XXIa) or (XXIb), $R^1$ and $R^2$ each represent a hydrogen atom, an amino group or a monovalent organic group having 1 to 20 carbon atoms. The organic group may preferably have 1 to 15 carbon atoms, and more preferably 1 to 10 carbon atoms. $R^3$ and $R^4$ each represent a divalent organic group having 1 to 20 carbon atoms, which may preferably have 2 to 15 carbon atoms, and more preferably 2 to 10 carbon atoms. $R^5$ represents a hydrogen atom or a monovalent organic group having 1 to 6 carbon atoms, and k and p represent an integer of 0 to 2 and an integer of 0 or 1, respectively.

In Formulas (XXIa) and (XXIb), the double bonds and positive electric charges are depicted in localized forms for the sake of convenience, to which, however, the present invention is by no means limited. The double bonds and positive electric charges (and the hydrogen atoms in the case when $R^1$ or $R^2$ is hydrogen) may be delocalized between the two nitrogen atoms of the amidine group. Also, depending on the structure of $R^3$ and $R^4$, they may be delocalized inside the heterocyclic ring constituted of these organic groups and the amidine group.

The resin composition containing the nitrogen-containing compound of the present invention may also be used as a molding material for encapsulation and a in multilayer or adhesive material. For example, epoxy resin compositions prepared using the nitrogen-containing compound of the present invention as a curing accelerator for epoxy resin and phenolic resin have superior rapid curability, curability after moisture absorption under moist condition, pot life and flow properties, and hence are suited as molding materials for encapsulation, laminate sheet materials and adhesive materials. Besides, such compositions may also be used in a wide field as, e.g., anisotropic conductive film materials and insulating materials. Accordingly, the present invention provides a resin curing accelerator containing the nitrogen-containing compound of the present invention.

In particular, a molding material making use of the nitrogen-containing compound of the present invention as the curing accelerator for epoxy resin and phenolic resin and compounded with a filler is suited for its use as a material for encapsulating electronic component devices. Accordingly, the present invention provides the epoxy resin composition containing the nitrogen-containing compound of the present invention and an electronic component device having device components encapsulated with the composition.

BEST MODES FOR PRACTICING THE INVENTION

A. Synthesis of Nitrogen-containing Compound

Figure 1:
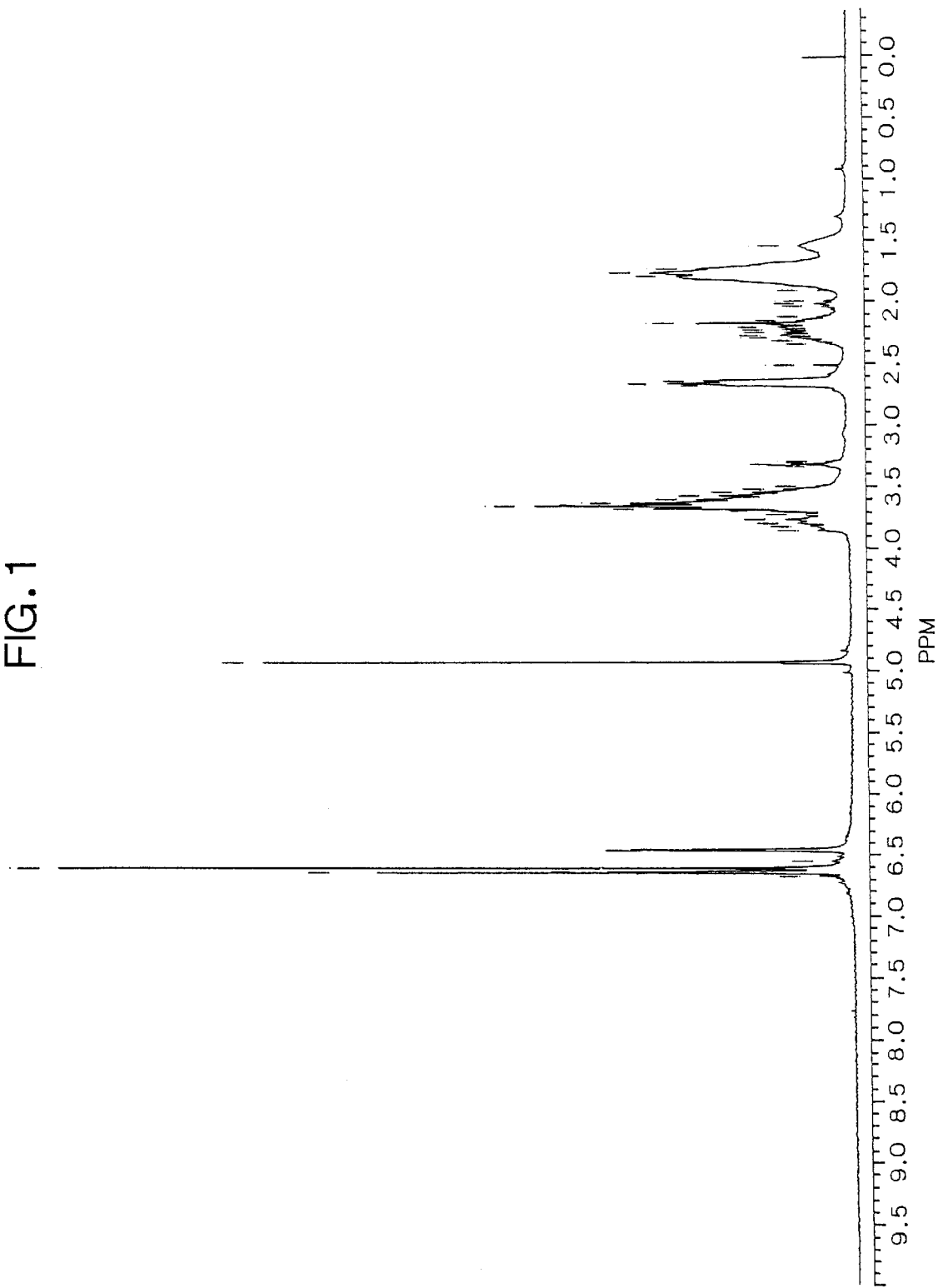
FIG. 1 shows a $^1$H-NMR spectrum of an addition product 1 obtained in Synthesis Example 1.

There are no particular limitations on the method of obtaining the nitrogen-containing compound of the present invention. For example, a method may be used in which an amidine compound (XXa) or (XXb) and a quinone compound (II) are subjected to addition reaction by mixing them with stirring in an organic solvent where the both are soluble or in a phenolic resin.

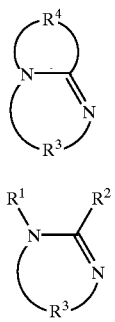

(XXa)

(XXb)

wherein $R^1$ and $R^2$ each represent a hydrogen atom, an amino group or a monovalent organic group having 1 to 20 carbon atoms; and $R^3$ and $R^4$ each represent a divalent organic group having 1 to 20 carbon atoms.

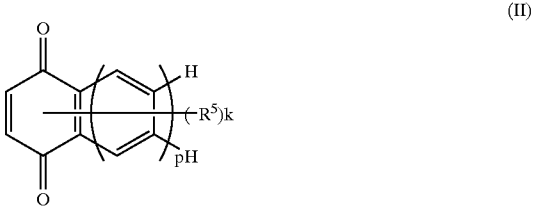

(II)

wherein $R^5$ represents a hydrogen atom or a monovalent organic group having 1 to 6 carbon atoms; and k and p represent an integer of 0 to 2 and an integer of 0 or 1, respectively.

The nitrogen-containing compound obtained by this addition reaction may include compounds represented by the following Formula (XXIa) or (XXIb).

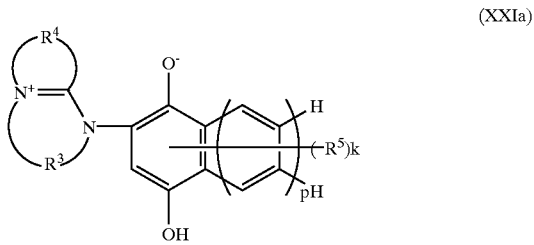

(XXIa)

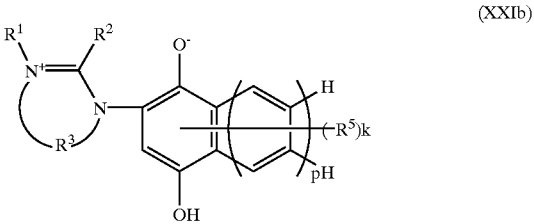

(XXIb)

wherein $R^1$ and $R^2$ each represent a hydrogen atom or a monovalent organic group having 1 to 20 carbon atoms; $R^3$ and $R^4$ each represent a divalent organic group having 1 to 20 carbon atoms; $R^5$ represents a hydrogen atom or a monovalent organic group having 1 to 6 carbon atoms; and k and p represent an integer of 0 to 2 and an integer of 0 or 1, respectively.

There are no particular limitations on the amidine compounds represented by the above Formula (XXa) or (XXb), which may include compounds represented by the following Formula (I), as exemplified by 1,8-diazabicyclo[5.4.0]undecene-7, 1,5-diazabicyclo[4.3.0]nonene-5, 6-dibutylamino-1,8-diazabicyclo[5.4.0]undecene-7 and 5,6-n-hexyl-1,8-diazabicyclo[5.4.0]undecene-7; 7-methyl-1,5,7-triazabicyclo[4.4.0]decene-5; and imidazole compounds such as imidazole, 2-methylimidazole, 4-methylimidazole, 2-ethyl-4-methylimidazole, 2-undecylimidazole, 2-heptadecylimidazole, 2-phenylimidazole, 1-benzyl-2-methylimidazole, 1-cyanoethyl-2-methylimidazole, 1-cyanoethyl-2-ethyl-4-methylimidazole, 1-cyanoethyl-2-undecylimidazole, 2-phenyl-4-methylimidazole, 1-cyanoethyl-2-phenylimidazole, 1-cyanoethyl-2-ethyl-4-methylimidazole, 2-phenyl-4-methyl-5-hydroxymethylimidazole, 2-phenyl-4,5-dihydroxymethylimidazole and 1-cyanoethyl-2-phenyl-4,5-di(cyanoethoxymethyl)imidazole.

Any of these may be used alone or in combination of two or more types. In particular, from the viewpoint of flow properties and reliability, the compounds represented by the following Formula (I) are preferred. In view of availability and cost, 1,8-diazabicyclo[5.4.0]undecene-7 and 1,5-diazabicyclo[4.3.0]nonene-5 are more preferred.

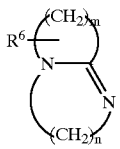
(I)

wherein $R^6$ is selected from a hydrogen atom and an alkyl group, a dialkyl-substituted amino group, an aryl group and an aralkyl group which have 1 to 12 carbon atoms; and m and n represent integers of 2 to 5 which are independent from each other.

There are no particular limitations on the quinone compound represented by the above Formula (II), which may include, e.g., 1,4-benzoquinone, 2,5-toluquinone, 1,4-naphthoquinone, 2,3-dimethylbenzoquinone, 2,6-dimethylbenzoquinone, 2,3-dimethoxy-5-methyl-1,4-benzoquinone, 2,3-dimethoxy-1,4-benzoquinone and phenyl-1,4-benzoquinone. Any of these may be used alone or in combination of two or more types. In particular, 1,4-benzoquinone and 2,5-toluquinone are preferred as being low-cost, being isolable in a high yield and exhibiting a good curability.

In the case when the reaction is carried out in an organic solvent, there are no particular limitations on the type of the organic solvent to be used, as long as the reaction is readily carried out. Such an organic solvent may include, e.g., ketone type solvents such as acetone, methyl ethyl ketone, cyclohexanone and methyl isobutyl ketone; aliphatic hydrocarbon type solvents such as n-hexane, cyclohexane and heptane; aromatic hydrocarbon type solvents such as toluene and xylene; ether type solvents such as diethyl ether, dimethoxyethane and diglyme; and alcohol type solvents such as methanol, ethanol, propanol and butanol. Any of these may be used alone or in the form of a mixture of two or more types. In particular, aromatic hydrocarbon type solvents such as toluene and xylene are preferred in order to isolate the resultant betaine compound in a good yield.

When the reaction is carried out, there are no particular limitations on the order of addition for the amidine compound and quinone compound. The amidine compound may be added to a solvent in which the quinone compound has been dissolved. This order of addition is preferred in order to isolate in a good yield the betaine compound, the addition product of the present invention.

There are no particular limitations on the mixing proportion of the quinone compound (II) to the amidine compound (XXa) or (XXb) [i.e., amount (mole) of quinone compound/amount of amidine compound (mole)]. From the viewpoint of an improvement in yield and a reduction in quantity of impurities, the proportion may preferably be so set as to be 2.6 to 2.0 (in molar ratio) in the case when the amidine compound has —NH— (i.e., in the case when the compound represented by the above Formula (XXb) is used and $R^1$ in the formula is hydrogen), and 1.3 to 1.0 in the cases other than that.

With regard to reaction temperature, there are no particular limitations thereon as long as it is not higher than the boiling point of the solvent used in the reaction. It may usually be from 0 to 50° C. Also, since the reaction is exothermic, the reaction temperature may preferably be controlled by cooling as occasion calls.

There are no particular limitations on reaction time. It is preferable for the addition reaction to be carried out for at least 1 hour after the addition of the amidine compound has been completed. Reaction for a time shorter than 1 hour may result in a low yield.

After the reaction, conventionally known means as exemplified by filtration, centrifugation and spray drying may be carried out to isolate the desired nitrogen-containing compound, the addition product.

The nitrogen-containing compound of the present invention may also be obtained by allowing the amidine compound and the quinone compound to react in a compound having a phenolic hydroxyl group or in a phenolic resin, as long as it does not affect the curing performance of epoxy resin compositions making use of it or the characteristics of electronic component devices.

In such a case, after the reaction, the product need not be isolated and may be used as it is, as a curing accelerator of the epoxy resin composition. This method, compared with the method in which the reaction is carried out in the presence of an organic solvent, enables omission of the procedure of isolating and purifying the addition product and can save production cost.

As to the compound having a phenolic hydroxyl group that is used in this reaction, there are no particular limitations thereon as long as it has a phenolic hydroxyl group, and known compounds having a phenolic hydroxyl group may be used. It may include, e.g., phenols such as phenol, cresol, xylenol, resorcinol, catechol, bisphenol A and bisphenol F; and naphthols such as α-naphthol, β-naphthol and dihydroxynaphthalene. Any of these may be used alone or in the form of a mixture of two or more types.

As to the phenolic resin, too, there are no particular limitations thereon as long as it has a phenolic hydroxyl group, and known phenolic resins may widely be used. It may include, e.g., resins obtained by subjecting a phenol such as phenol, cresol, xylenol, resorcinol, catechol, bisphenol A or bisphenol F or a naphthol such as α-naphthol, β-naphthol or dihydroxynaphthalene and an aldehyde such as formaldehyde, acetaldehyde, propionaldehyde, benzaldehyde or salicylaldehyde to condensation or cocondensation in the presence of an acid catalyst; and paraxylylene modified phenolic resins, metaxylylene/paraxylylene modified phenolic resins, melamine modified phenolic resins, terpene modified phenolic resins, dicyclopentadiene modified phenolic resins, cyclopentadiene modified phenolic resins, and polycyclic aromatic-ring modified phenolic resins. Any of these may be used alone or in the form of a mixture of two or more types. These phenolic resins are usable without limitations on their molecular weight, softening point, hydroxyl group equivalent weight and so forth.

When the reaction is carried out, there are no particular limitations on the order of addition for the amidine compound and quinone compound. From the viewpoint of the yield of the nitrogen-containing compound, the amidine compound may be added to the compound having a phenolic hydroxyl group or phenolic resin in which the quinone compound has been dissolved. Such order of addition is preferred.

There are no particular limitations on the mixing proportion of the quinone compound (II) to the amidine compound (XXa) or (XXb) used in this reaction [i.e., amount (mole) of quinone compound/amount of amidine compound (mole)]. From the viewpoint of an improvement in yield and a reduction in quantity of impurities, the proportion may preferably be so set as to be 2.6 to 2.0 (in molar ratio) in the case when the amidine compound has —NH— (i.e., in the case when the compound represented by the above Formula (XXb) is used and $R^1$ in the formula is hydrogen), and 1.3 to 1.0 in the cases other than that. If the amidine compound is mixed in a larger quantity than the quinone compound, any residual amidine compound may form a salt with the compound having a phenolic hydroxyl group or the phenolic resin, so that epoxy resin compositions incorporated with such a compound may have a low curability after moisture absorption under moist condition.

With regard to reaction temperature, there are no particular limitations thereon as long as it is temperature at which the compound having a phenolic hydroxyl group or phenolic resin used in the reaction stands liquid. It may usually be from 100 to 150° C. Since the reaction is exothermic, the reaction temperature may preferably be controlled by cooling as occasion calls.

There are no particular limitations on reaction time. It is preferable for the reaction to be carried out for at least 1 hour after the addition of the amidine compound has been completed. Reaction for a time shorter than 1 hour may make the amidine compound non-uniform.

The reaction product thus obtained may be cooled, followed by pulverization, and is usable as a curing agent containing as a curing accelerator the nitrogen-containing compound of the present invention.

The nitrogen-containing compound represented by the above Formula (XXIa) may include, e.g., compounds represented by the following Formula (VII). In particular, those in which $R^6$ is hydrogen or an alkyl group having 1 to 6 carbon atoms, k and p are each 0, m is 3 or 5 and n is 3 are preferred.

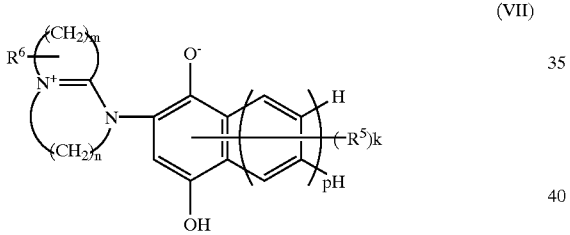

(VII)

wherein $R^6$ in Formula (VII) is selected from a hydrogen atom, and an alkyl group, a dialkyl-substituted amino group, an aryl group, an alkyl group and an aralkyl group having 1 to 12 carbon atoms; $R^5$ represents a hydrogen atom and an alkyl group, an alkoxyl group, an aryl group and an aralkyl group which have 1 to 6 carbon atoms; k and p represent an integer of 0 to 2 and an integer of 0 or 1, respectively; and m and n represent integers of 2 to 5 which are independent from each other.

Such addition products may include, e.g., structures represented by the following Formulas (VIII) to (XVII) and (XXII).

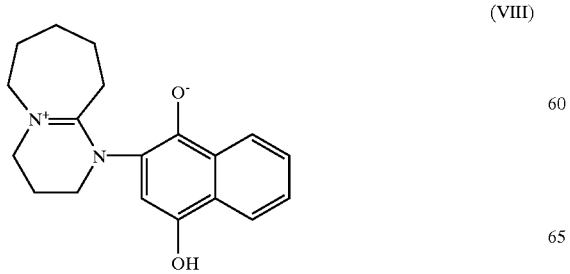

(VIII)

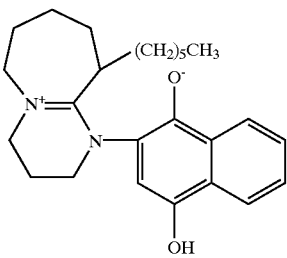

(IX)

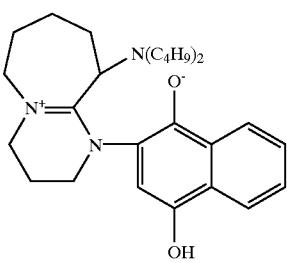

(X)

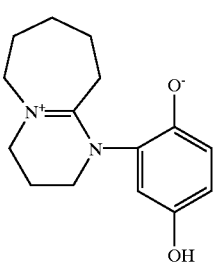

(XI)

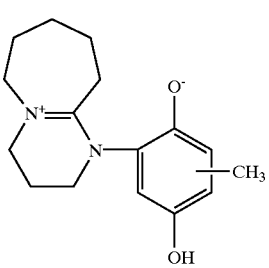

(XII)

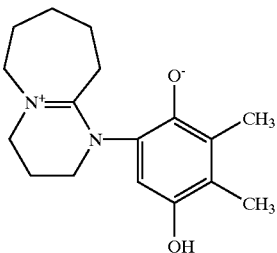

(XIII)

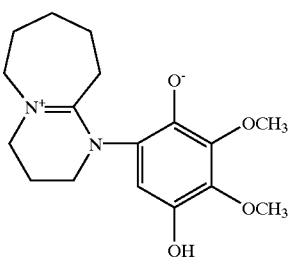

(XIV)

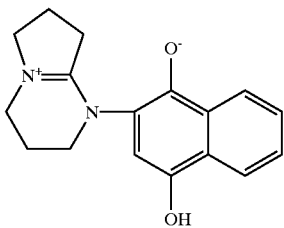 (XV)

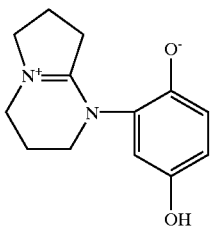 (XVI)

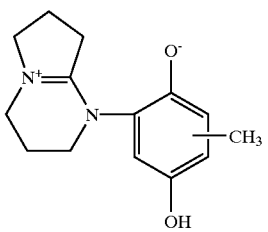 (XVII)

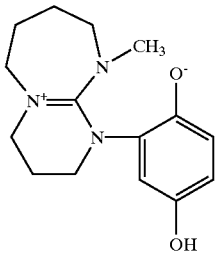 (XXII)

The addition product represented by the above Formula (XXIa) or (XXIb) may include, e.g., structures represented by the following Formulas (XXIII) to (XXVIII).

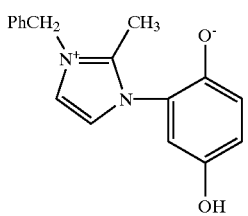 (XXIII)

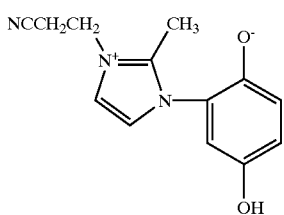 (XXIV)

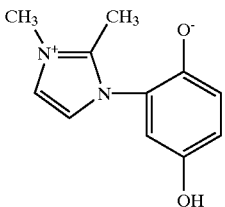 (XXV)

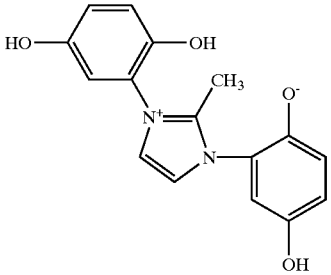 (XXVI)

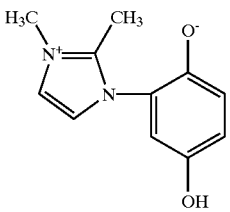 (XXVII)

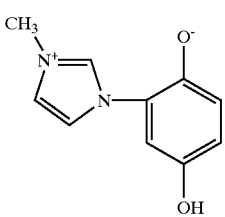 (XXVIII)

B. Resin Composition/Encapsulation Molding Material

The resin composition of the present invention contains the above nitrogen-containing compound of the present invention (herein "component (A)") and may further appropriately contain the following components (1) to (6) as occasion calls. The respective components are specifically described below.

Incidentally, the resin composition of the present invention may be prepared by any methods as long as the materials of various types can uniformly be dispersed and be mixed. A commonly available preparation method may include a method in which materials formulated in prescribed quantities are thoroughly mixed by means of a mixer and the mixture obtained is melt-kneaded by means of a mixing roll or an extruder, followed by cooling and then pulverization. For example, it can be obtained by stirring and mixing the following components (1) to (6) uniformly in prescribed quantities and kneading the resultant mixture by means of a kneader, roll mill or extruder previously heated to 70 to 140° C., followed by cooling and then pulverization. The product obtained may be made into tablets in such a size and weight that may suit to molding conditions, so as to be usable with ease.

(1) Epoxy Resin:

The epoxy resin usable in the resin composition of the present invention (herein "component (B)") may be any of epoxy resins commonly used. There are no particular limitations. It may include;

glycidyl type (inclusive of methyl glycidyl type) epoxy resins as exemplified by glycidyl ethers of phenols such as bisphenol A, bisphenol F, resorcinol, phenol novolak and cresol novolak; glycidyl ethers of alcohols such as butanediol, polyethylene glycol and polypropylene glycol; glycidyl esters of carboxylic acids such as phthalic acid, isophthalic acid and tetrahydrophthalic acid; and aniline or isocyanuric acid an active hydrogen bonded to the nitrogen atom whose has been substituted with a glycidyl group;

what is called alicyclic epoxy resins obtained by epoxidizing the olefinic bond in the molecule, such as vinylcyclohexene diepoxide, 3,4-epoxycylcohexylmethyl-3,4-epoxycylcohexane carboxylate, and 2-(3,4-epoxy)cyclohexyl-5,5-spiro(3,4-epoxy)cyclohexane-m-dioxane; and glycidyl ethers of paraxylylene modified phenolic resins, glycidyl ethers of metaxylylene/paraxylylene modified phenolic resins, glycidyl ethers of terpene modified phenolic resins, glycidyl ethers of dicyclopentadiene modified phenolic resins, glycidyl ethers of cyclopentadiene modified phenolic resins, glycidyl ethers of polycyclic aromatic-ring modified phenolic resins, glycidyl ethers of naphthalene-ring-containing phenolic resins, biphenyl type epoxy resins, and halogenated phenol novolak type epoxy resins.

Any of these may be used alone or in the form of a mixture of two or more types.

In particular, epoxy resins represented by the following Formula (III) or (IV) are preferred in view of flow properties and reflow resistance, and 4,4'-bis(2,3-epoxypropoxy)-3,3',5,5'-tetramethylbiphenyl is more preferred.

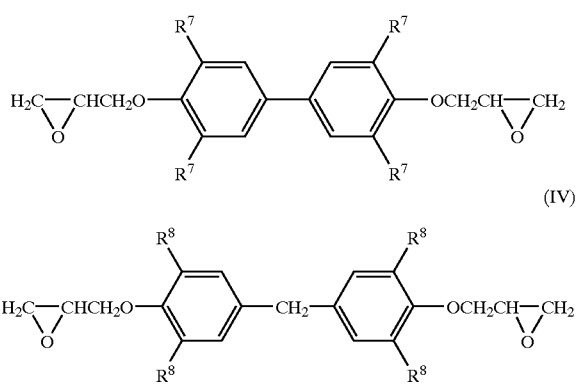

wherein $R^7$ and $R^8$ each represent a hydrogen atom or a methyl group.

These epoxy resins of the Formulas (III) and (IV) may each be used alone or mutually in combination. In order for their performance to be exhibited, they may preferably be used in an amount of at least 60% by weight in total based on the total weight of the epoxy resin.

(2) Phenolic Resin:

A phenolic resin having at least two phenolic hydroxyl groups in one molecule, used in the resin composition of the present invention (herein "component (C)") acts as a curing agent of the epoxy resin. There are no particular limitations thereon and conventionally known curing agents may widely be used. For example, it may include resins obtained by subjecting a phenol such as phenol, cresol, xylenol, resorcinol, catechol, bisphenol A or bisphenol F or a naphthol such as α-naphthol, β-naphthol or dihydroxynaphthalene and an aldehyde such as formaldehyde, acetaldehyde, propionaldehyde, benzaldehyde or salicylaldehyde to condensation or cocondensation in the presence of an acid catalyst; and paraxylylene modified phenolic resins, metaxylylene/paraxylylene modified phenolic resins, melamine modified phenolic resins, terpene modified phenolic resins, dicyclopentadiene modified phenolic resins, cyclopentadiene modified phenolic resins, and polycyclic aromatic-ring modified phenolic resins. Any of these may be used alone or in the form of a mixture of two or more types.

These phenolic resins are usable without limitations on their molecular weight, softening point, hydroxyl group equivalent weight and so forth. In particular, those represented by the following Formula (V) or (VI) are preferred in view of curability. In the case when the 4,4'-bis(2,3-epoxypropoxy)-3,3'1'5,5'-tetramethylbiphenyl is used as the epoxy resin, the structure of Formula (V) is preferred from the viewpoint of a low moisture absorption and a curability.

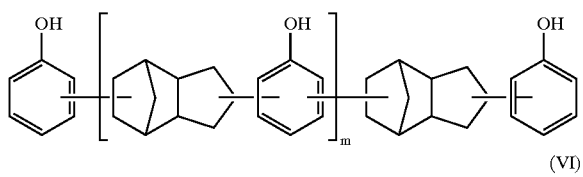

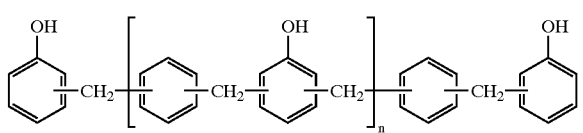

These phenolic resins of the Formulas (V) and (VI) may each be used alone or in combination of the both. In order for their performance to be exhibited, they may preferably be used in an amount of at least 60% by weight in total based on the total weight of the epoxy resin. There are no particular limitations on the mixing proportion when the both are used in combination. It is preferable for (V)/(VI) to be set in the range of from 0.5 to 3.

Letter symbols m and n in the formulas each represent a number of 0 to 10. If these are each more than 10, the component-(C) phenolic resin has a high melt viscosity and hence the epoxy resin composition also has a high viscosity at the time of its melt molding, tending to cause faulty filling and deformation of bonding wires (i.e., gold wires which connect device components with leads). Hence, m and n must each be in the range of from 0 to 10, and may each more preferably be in the range of from 1 to 4 on the average in one molecule.

In the present invention, with regard to the mixing proportion between the component-(B) epoxy resin and the component-(C) phenolic resin, the proportion of hydroxyl group equivalent weight of the phenolic resin to epoxy group equivalent weight of the epoxy resin, (C)/(B), may preferably be set in the range of from 0.5 to 2.0, more preferably from 0.7 to 1.5, and still more preferably from 0.8 to 1.3. If it is less than 0.5, the epoxy resin may cure insufficiently to tend to make cured products have poor heat resistance, moisture resistance and electrical properties. If on the other hand it is more than 1.5, the phenolic resin component is so excessive that phenolic hydroxyl groups may remain in the cured resin in a large quantity, tending to result in poor electrical properties and moisture resistance.

(3) Curing Accelerator:

The nitrogen-containing compound of the present invention, used in the resin composition of the present invention, acts as a curing accelerator for accelerating the curing reaction of epoxy groups of the epoxy resin with phenolic hydroxyl groups of the phenolic resin. As this curing accelerator, the nitrogen-containing compound of the present invention may be used alone, or the nitrogen-containing compound of the present invention may be used in the form of a mixture of two or more types. It may also be used in combination with at least one of other conventionally known curing accelerators.

The curing accelerator usable in combination with the nitrogen-containing compound of the present invention may include, e.g., diazabicycloalkenes such as 1,8-diaza-bicyclo(5,4,0)undecene-7, and derivatives thereof; phenol novolak salts of diazabicycloalkenes such as 1,8-diaza-bicyclo(5,4,0)undecene-7, and those of derivatives thereof; tertiary amines such as triethylenediamine, benzyldimethylamine, triethanolamine, dimethylaminoethanol and tris(dimethylaminomethyl)phenol; imidazoles such as 2-methylimidazole, 2-phenylimidazole, 2-phenyl-4-methylimidazole and 2-heptadecylimidazole; tetra-substituted-phosphonium tetra-substituted borates such as tetraphenylphosphonium tetraphenyl borate; tetraphenylboron salts such as 2-ethyl-4-methylimidazole tetraphenyl borate and N-methylmorpholine tetraphenyl borate; organophosphines such as triphenylphosphine, diphenyl(p-tolyl) phosphine, tris(alkylphenyl)phosphines, tris(alkoxyphenyl)phosphines, tris(alkylalkoxyphenyl)phosphines, tris(dialkyiphenyl)phosphines, tris(trialkylphenyl)phosphines, tris(tetraalkylphenyl)phosphines, tris(dialkoxyphenyl)phosphines, tris(trialkylalkoxyphenyl)phosphines and tris(tetraalkylphenyl)phosphines, or complexes of any of these organophosphines with organoborons; and addition products of organophosphines with quinones, such as betaine type addition products of triphenylphosphine with p-quinone and betaine type addition products of diphenyl(p-tolyl) phosphine with p-quinone.

When any of these curing accelerators are used in combination, the component (A) may preferably be mixed in an amount not less than 30% by weight, and more preferably not less than 50% by weight, based on the total weight of the curing accelerator. In resin compositions making use of the component-(B) epoxy resin and the component-(C) phenolic resin, there are disadvantages that the above tertiary amines make moisture resistance and storage stability poor as compared with the case when the component (A) is used, and the organophosphines tend to be affected by oxidation to provide a low curability. Use of the tetraphenyl boron salts tends to bring about a disadvantage in adhesion. Hence, the present invention can be less effective if the component (A) is mixed in an amount less than 30% by weight.

On the total weight of the curing accelerators inclusive of the component (A), there are no particular limitations as long as they are mixed in an amount necessary for achieving the curing acceleration effect. They may preferably be in an amount of from 0.1 to 10 parts by weight, and more preferably from 0.3 to 5.0 parts by weight, based on 100 parts by weight of the total weight of the component-(B) epoxy resin and the component-(C) phenolic resin. If they are in an amount less than 0.1 part by weight, the curing can not be made in a short time, and, in an amount more than 10 parts by weight, the curing rate may be too high to obtain good molded products.

(4) Inorganic Filler:

The resin composition of the present invention may optionally be incorporated with an inorganic filler in order to lower moisture absorption and coefficient of linear expansion, to improve thermal conductivity and to improve strength. Especially when used as the encapsulation molding material, it is desirable for the molding material to contain the inorganic filler.

The inorganic filler usable in the present invention (herein "component (D)") may include fine powders of fused silica, crystal silica, glass, alumina, calcium carbonate, zirconium silicate, calcium silicate, silicon nitride, aluminumnitride, boron nitride, beryllia, zirconia, zircon, forsterite, steatite, spinel, mullite, titania, talc, clay and mica, or sphered beads of any of these. Also, as an inorganic filler having a flame-retardant effect, it may include aluminum hydroxide, magnesium hydroxide and zinc borate. Any of these may be used alone or in combination of two or more. Of the foregoing inorganic fillers, fused silica is preferred from the viewpoint of lowering the coefficient of linear expansion, and alumina from the viewpoint of a high thermal conductivity.

In the case when the inorganic filler is incorporated, it may preferably be mixed in an amount ranging from 55 to 90% by volume of the total weight of the resin composition. Since the inorganic filler is added for the purpose of improving the coefficient of linear expansion, thermal conductivity, modulus of elasticity and so forth of cured products, its mixing in an amount less than 55% by volume can not bring about any sufficient improvement of these characteristics, and, in an amount more than 90% by volume, the resin composition may have a very high viscosity to have low flow properties, tending to make it difficult to carry out molding.

The component-(D) inorganic filler may also preferably have an average particle diameter ranging from 1 to 50 $\mu$m, and particularly preferably from 10 to 30 $\mu$m. If it has an average particle diameter smaller than 1 $\mu$m, the resin composition tends to increase in viscosity. If it has an average particle diameter larger than 50 $\mu$m, the resin component and the filler tend to separate from each other, so that the cured product tends to be non-uniformly formed or have varied properties and also any narrow gaps in a mold tend to be low filled.

From the viewpoint of flow properties, the component-(D) inorganic filler may preferably have a particle shape which is spherical rather than rectangular, and may preferably have a particle size distribution in a wide range. For example, when the filler is mixed in an amount of 75% by volume or more, 75% by volume or more of the particles may preferably be spherical and be size-distributed in a wide range of from 0.1 to 80 $\mu$m. Such a filler can readily provide a excellent fill structure, and hence may cause less increase in viscosity of materials even when mixed in a large quantity, so that compositions having superior flow properties can be obtained.

(5) Anion Exchanger:

When the epoxy resin composition of the present invention is used as the encapsulation molding material, it is preferable to add an anion exchanger, component (E), from the viewpoint of an improvement in moisture resistance of electronic component devices having device components to be encapsulated. The moisture resistance taken into account here is the moisture resistance reliability of electronic component devices such as IC packages, and is especially intended for a moisture resistance test made under application of voltage, such as a bias type high-temperature high-humidity test and HAST (a highly accelerated humidity and stress test).

Faults that may occur in these moisture resistance tests are mostly disconnections caused by corrosion of aluminum wirings formed on device components of ICs. The use of the epoxy resin composition comprised of the component-(A) curing accelerator of the present invention, the component-(B) epoxy resin, the component-(C) phenolic resin and the component-(D) inorganic filler mixed in a specific quantity makes it possible to attain a good moisture resistance reliability. However, in order to attain a much superior voltage application type moisture resistance, it is effective to add the anion exchanger.

In the case of voltage application type moisture resistance tests, the anode-side aluminum wirings especially tend to corrode. This is presumed to be caused by the following phenomenon: The anode-side wirings or bonding pads, when water is present, undergo anodic oxidation due to oxygen generated by electrolysis of the water and stable aluminum oxide films are formed on their surfaces. Hence, any corrosion of aluminum should not proceed. However, any presence of halide ions such as chloride ions even in a trace quantity solubilizes the aluminum oxide films to cause pitting corrosion in which the underlying aluminum dissolves. This pitting corrosion on the anode side proceeds faster than grain boundary corrosion on the cathode side, and hence, in the voltage application type moisture resistance tests, the anode-side aluminum wiring corrosion proceeds in advance to cause faults. Accordingly, in order to prevent such corrosion on the anode side, it is effective to add an anion exchanger capable of capturing halide ions present in a trace quantity.

There are no particular limitations on anion exchangers usable in the present invention, which may preferably be hydrotalcites represented by the following Formula (XVIII):

$$Mg_{1-X}Al_X(OH)_2(CO_3)_{X/2}\cdot mH_2O \quad \text{(XVIII)}$$

(0<X≦0.5; m is a positive number) and hydrated oxides of elements selected from magnesium, aluminum, titanium, zirconium and bismuth. Any of these may be used alone or in combination of any number of types.

The hydrotalcites are compounds having the property to capture anions such as halide ions upon replacement with $CO_3$ in the structure, and not to release the halide ions incorporated in crystal structure, until the crystal structure destroys at about 350° C. or above. To exemplify hydrotalcites having such property, they may include $Mg_6Al_2(OH)_{16}CO_3 \cdot 4H_2O$, produced as a natural product, and as a synthetic product $Mg_{4.3}Al_2(OH)_{12.6}CO_3 \cdot mH_2O$.

The epoxy resin composition of the present invention is affected by the component (C) phenolic resin, and an extract of its cured product with pure water shows an acidity with a pH value of 3 to 5. Hence, an environment that is corrosive for the amphoteric metal aluminum is provided. Since, however, the hydrotalcites also have the action to adsorb acid, they also act to bring the extract near to the neutral side. Thus, the effect of this action can be presumed to be also a factor by which the addition of a hydrotalcite works effectively on the prevention of the corrosion of aluminum.

The hydrated oxides of elements selected from magnesium, aluminum, titanium, zirconium and bismuth can also capture halide ions upon replacement with hydroxide ions, and these ion exchangers further exhibit a good ion exchange ability on the acid side. With regard to the encapsulation epoxy resin molding material of the present invention, its extract stands on the acid side as stated above, and hence these hydrated oxides are also effective especially for the prevention of the corrosion of aluminum. To exemplify these, they may include hydrated oxides such as $MgO \cdot nH_2O$, $Al_2O_3 \cdot nH_2O$, $TiO_2 \cdot nH_2O$, $ZrO_2 \cdot nH_2O$ and $Bi_2O_3 \cdot nH_2O$.

There are no particular limitations on the amount of any of these anion exchangers to be mixed, as long as it is an amount sufficient for capturing the anions such as halide ions. It may preferably be set in the range of from 0.1 to 30 parts by weight, and more preferably from 1 to 5 parts by weight, based on 100 parts by weight of the component-(B) epoxy resin.

(6) Other Additives:

As other additives, the resin composition of the present invention may optionally be incorporated with a coupling agent for improving adhesion between the resin component and the filler, a colorant for giving color, a release agent for providing a good releasability to a mold at the time of molding, a flame retardant for imparting flame retardance, a stress relaxation agent and so forth.

As the coupling agent, usable are known additives including silane compounds such as epoxysilane, mercaptosilane, aminosilane, alkylsilane, ureidosilane and vinylsilane, titanium compounds, aluminum chelates, and aluminum/zirconium compounds.

As the colorant, usable are known compounds such as carbon black, organic dyes, organic pigments, titanium oxide, red lead and red iron oxide. As the stress relaxation agent, usable are silicone oil and silicone rubber powder.

As the flame retardant, usable are known organic or inorganic compounds containing a halogen atom, an antimony atom, a nitrogen atom or a phosphorus atom, and metal hydroxides, as exemplified by brominated epoxy resin and antimony trioxide. The flame retardant may preferably be mixed in a proportion of from 1 to 30 parts by weight, and more preferably from 2 to 15 parts by weight, based on 100 parts by weight of the component-(B) epoxy resin.

As the release agent, usable are an oxide type or non-oxide type polyolefin, carnauba wax, montanate, montanic acid and stearic acid.

As the release agent, the oxide type or non-oxide type polyolefin may preferably be added in an amount of from 0.01 to 10 parts by weight, and more preferably from 0.1 to 5 parts by weight, based on 100 parts by weight of the component-(B) epoxy resin. If it is in an amount less than 0.01 part by weight, any sufficient releasability is not obtainable. If it is in an amount more than 10 parts by weight, there is a possibility of deteriorating adhesion.

Such an oxide type or non-oxide type polyolefin may include low-molecular-weight polyethylene having number-average molecular weight of about 500 to about 10,000, such as H4, PE or PED series available from Hoechst Corp.

Besides this polyolefin, at least one of conventionally known release agents such as carnauba wax, montanate, montanic acid and stearic acid may also be used in combination. When any of these additional release agent is used in combination in addition to the oxide type or non-oxide type polyolefin, it may preferably be mixed in a proportion of from 0.1 to 10 parts by weight, and more preferably from 0.5 to 3 parts by weight, based on 100 parts by weight of the component-(B) epoxy resin.

C. Electronic Component Device

The electronic component device of the present invention can be produced by mounting active components such as semiconductor chips, transistors, diodes or thyristors and passive components such as capacitors, resistors or coils on a support member such as a lead frame, a tape carrier having been wired, a wiring board, glass or a silicon wafer, and encapsulating necessary portions with the resin composition of the present invention. As methods of encapsulation for the electronic component device, low-pressure transfer molding is most commonly used. Injection molding or compression molding may also be used.

Such electronic devices of the present invention may include commonly available resin-encapsulated ICs in which semiconductor components are fastened onto a lead frame, and terminals (such as bonding pads) and leads of each device component are connected by wire bonding or through bumps, followed by encapsulation with the epoxy resin composition by transfer molding or the like. To exemplify such devices, they may include DIP (dual-inline package), PLCC (plastic-leaded chip carrier), QFP (quad flat package), SOP (small outline package), SOJ (small outline J-lead package), TSOP (thin small outline package) and TQFP (thin quad flat package). Especially when applied to electronic component devices assembled on wiring boards by surface mounting, the resin composition of the present invention can exhibit a superior reliability.

The device components to be encapsulated, as long as they have the form of resin-encapsulated packages having leads (external connecting terminals) as shown above, may cover not only semiconductor components such as transistors, thyristors, ICs, LSIs and diodes, but also resistors, resistance arrays, capacitors, and switches such as poly-switches. A superior reliability can be provided also for these device components. At the same time, a superior reliability can be achieved also for hybrid ICs fabricated by mounting various device components and electronic parts on a ceramic substrate and thereafter encapsulating the whole.

A superior reliability can further be achieved also for BGAs (ball grid arrays) and CSPs (chip size packages) in which device components are mounted on an organic substrate on the back of which terminals for wiring-board connection have been formed, and the device components are connected through bumps or by wire bonding, to wirings formed on the organic substrate, followed by encapsulation with the epoxy resin composition. The resin composition of the present invention is also effectively usable in the manufacture of printed circuit boards. TCPs (tape carrier packages) in which semiconductor chips bonded to a tape carrier through bumps are encapsulated with the molding material of the present invention may also be given as the electronic component device of the present invention.

EXAMPLES

Synthesis examples and working examples of the present invention will be given below in detail with reference to drawings. The present invention is by no means limited to these.

Synthesis Example 1

Synthesis of Addition Product 1:

Into a 3-litter four-necked flask having a thermometer, a stirrer and a dropping funnel, toluene (2,000 ml) and 1,4-benzoquinone (220 g) were put. These were stirred to dissolve the benzoquinone, and thereafter a mixture of 1,8-diazabicyclo[5.4.0]undecene-7 (282 g) was added dropwise over a period of 3.5 hours while cooling and stirring the solution appropriately so as not to have a temperature higher than 40 degrees. After its addition was completed, the reaction mixture was further stirred for 12 hours at room temperature. Subsequently, the solid formed was collected by filtration by suction, followed by washing with toluene (1,500 ml) andthenn-hexane (1,000 ml). The resultant solid was dried under reduced pressure to obtain a greenish brown powder (446 g). Elementary analysis of the powder thus obtained revealed that C was 69.20, H was 7.74 and N was 10.76 as calculated values (%) and C was 68.95, H was 7.62 and N was 10.91 as found values (%).

Figure 2:
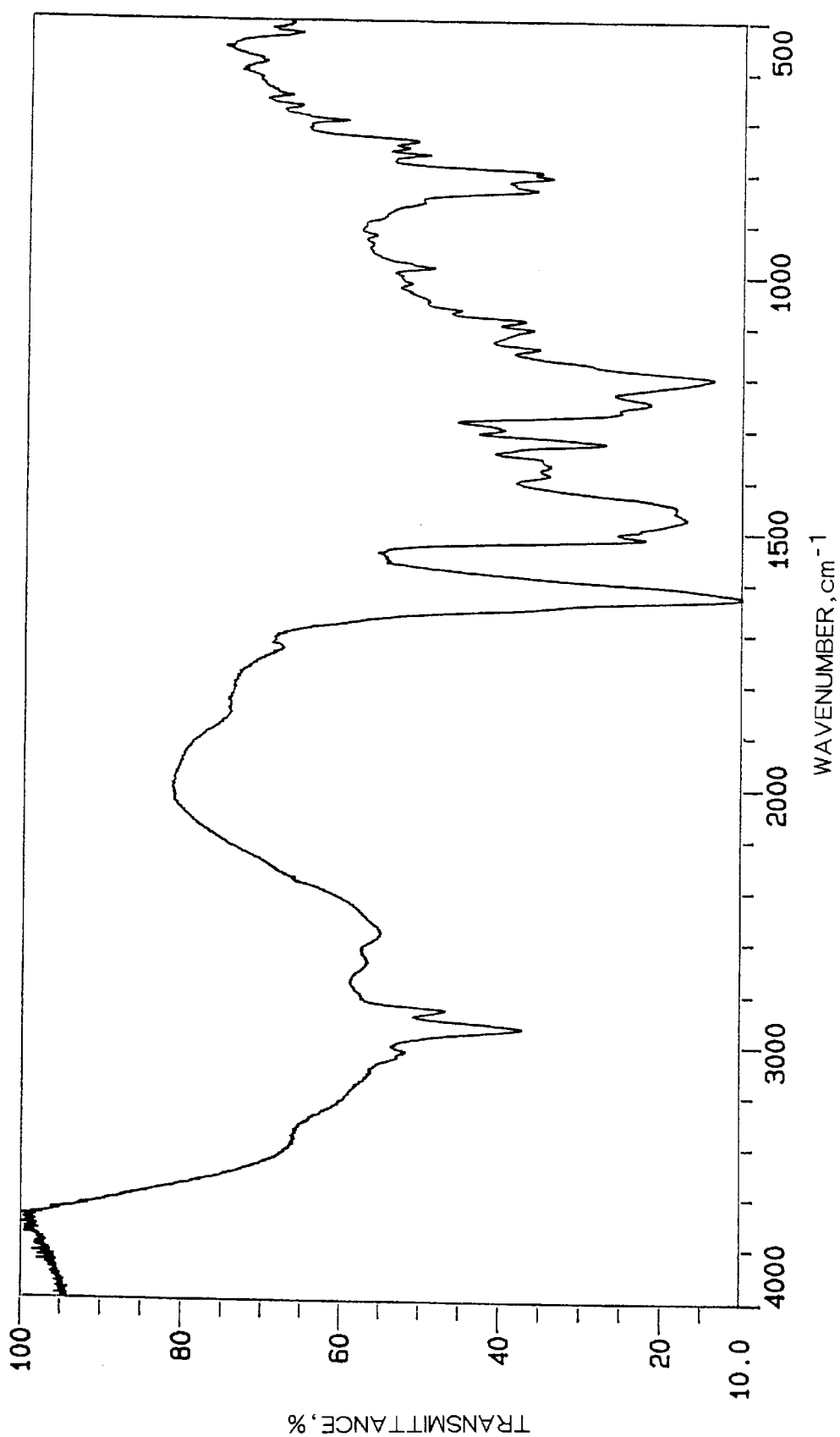
FIG. 2 shows an IR spectrum of the addition product 1 obtained in Synthesis Example 1.

From these results of elementary analysis, a $^1$H-NMR spectrum (measuring solvent: methanol-$d_4$) shown in FIG. 1 and an IR spectrum (KBr method) shown in FIG. 2, it was ascertained that a nitrogen-containing compound represented by the following structural formula (XI) (herein "addition product 1") was obtained by the addition of the amidine compound with the quinone compound.

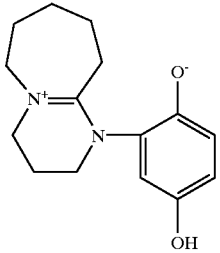

(XI)

Synthesis Example 2

Synthesis of Addition Product 2:

Into a 3-litter four-necked flask having a thermometer, a stirrer and a dropping funnel, toluene (2,000 ml) and 2,5-toluquinone (269 g) were put. These were stirred to dissolve the 2,5-toluquinone, and thereafter a mixture of 1,8-diazabicyclo[5.4.0]undecene-7 (305 g) was added dropwise over a period of 3.5 hours while cooling and stirring the solution appropriately so as not to have a temperature higher than 40 degrees. After its addition was completed, the reaction mixture was further stirred for 12 hours at room temperature. Subsequently, the solid formed was collected by filtration by suction, followed by washing with toluene (1,000 ml) and then n-hexane (500 ml). The resultant solid was dried under reduced pressure to obtain a brown powder (483 g). Elementary analysis of the powder thus obtained revealed that C was 70.04, H was 8.08 and N was 10.21 as calculated values (%) and C was 70.11, H was 7.88 and N was 9.98 as found values (%).

Figure 3:
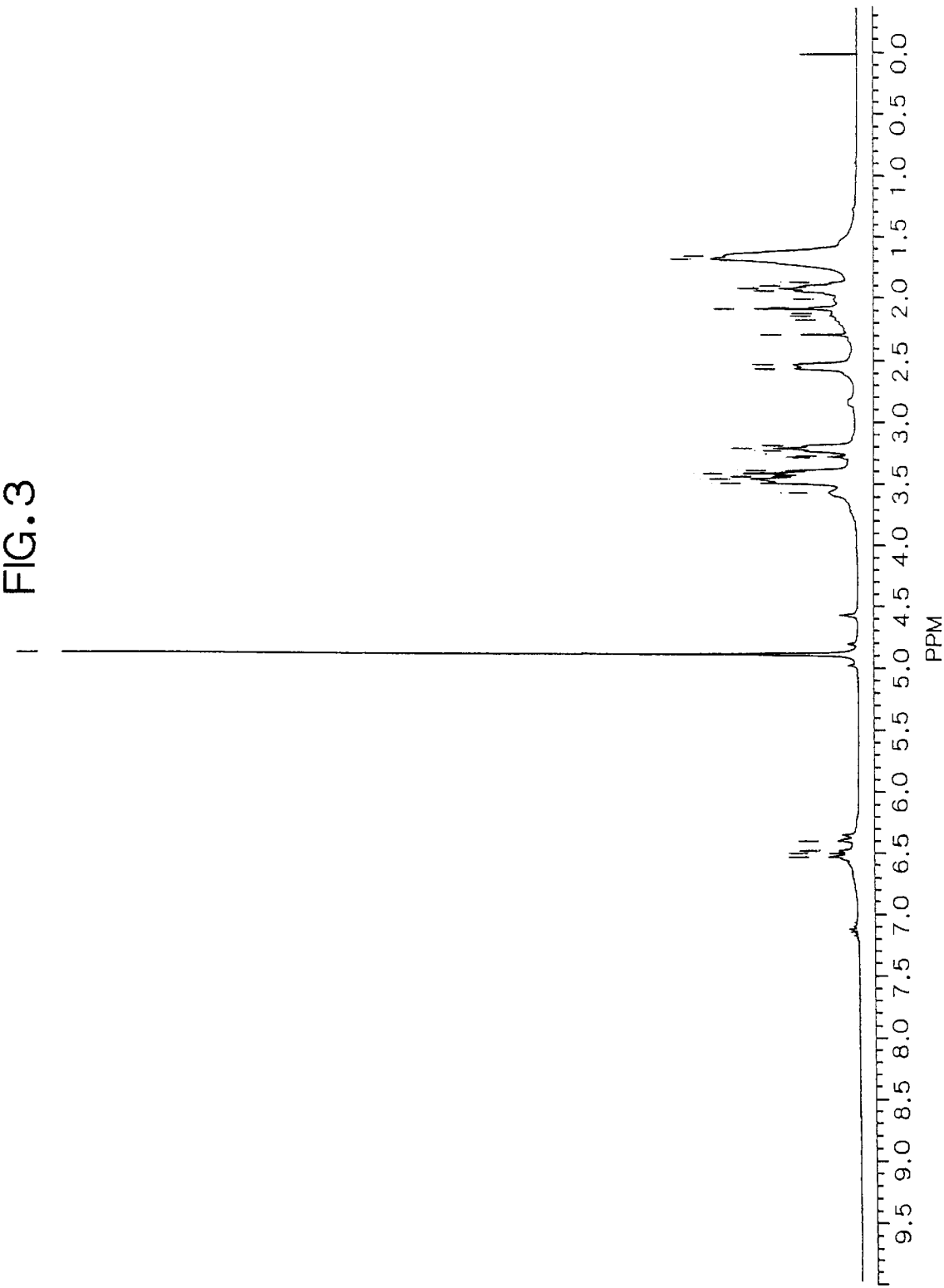
FIG. 3 shows a $^1$H-NMR spectrum of an addition product 2 obtained in Synthesis Example 2.
Figure 4:
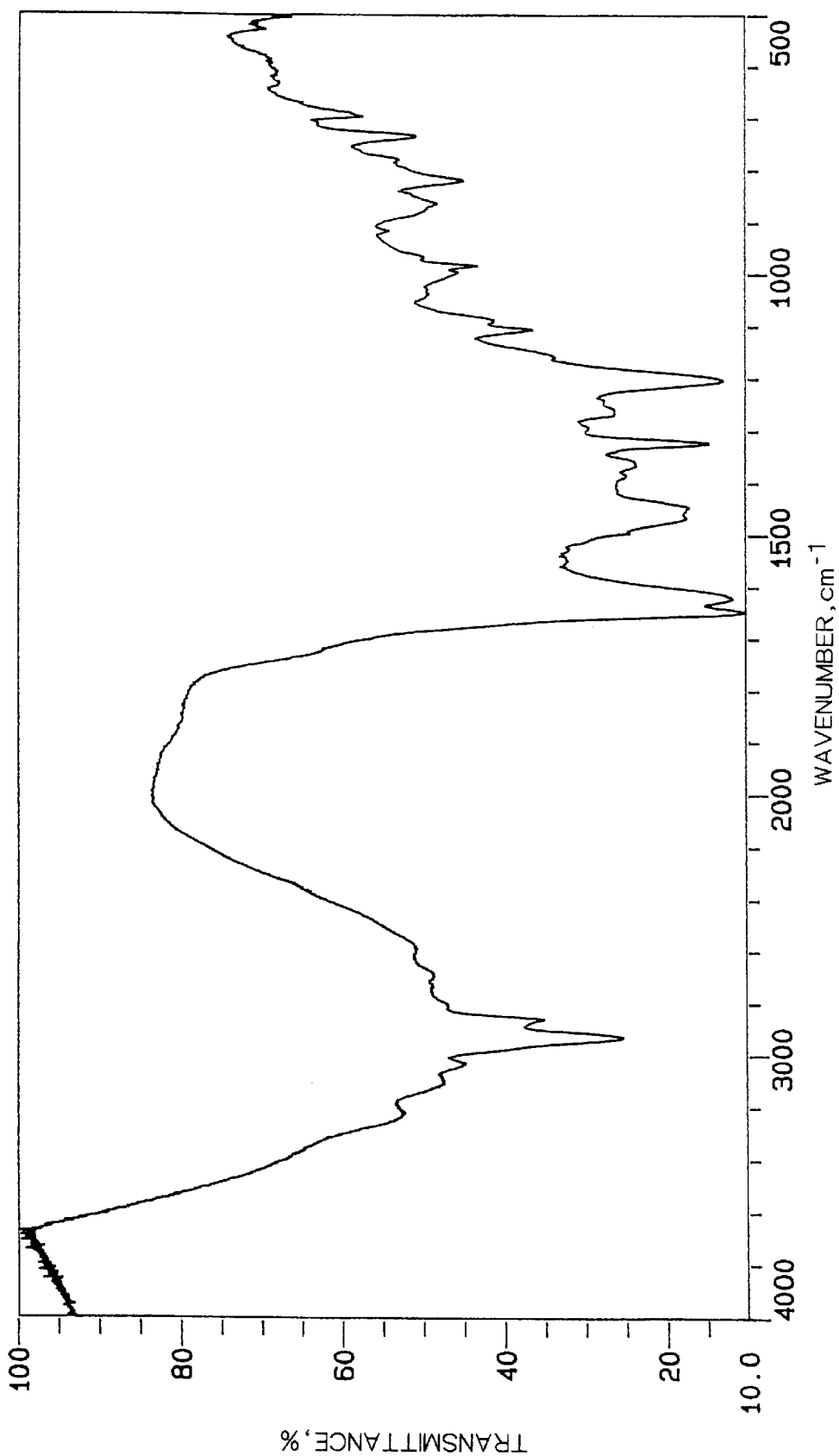
FIG. 4 shows an IR spectrum of the addition product 2 obtained in Synthesis Example 2.

From these results of elementary analysis, a $^1$H-NMR spectrum (measuring solvent: methanol-$d_4$) shown in FIG. 3 and an IR spectrum (KBr method) shown in FIG. 4, it was ascertained that a nitrogen-containing compound represented by the following structural formula (XII) (herein "addition product 2") was obtained by the addition of the amidine compound with the quinone compound according to the present invention.

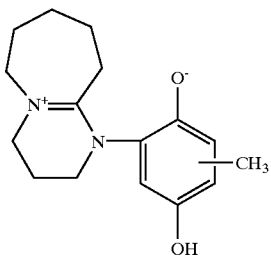

(XII)

Synthesis Example 3

Synthesis of Addition Product 3:

Into a 3-litter four-necked flask having a thermometer, a stirrer and a dropping funnel, toluene (2,000 ml) and 1,4-benzoquinone (220 g) were put. These were stirred to dissolve the benzoquinone, and thereafter a mixture of 1,5-diazabicyclo[4.3.0]nonene-5 (230 g) was added dropwise over a period of 3.5 hours while cooling and stirring the solution appropriately so as not to have a temperature higher than 40 degrees. After its addition was completed, the reaction mixture was further stirred for 12 hours at room a temperature. Subsequently, the solid formed was collected by filtration by suction, followed by washing with toluene (1,000 ml) and then n-hexane (500 ml). The resultant solid was dried under reduced pressure to obtain a brown powder (398 g). Elementary analysis of the powder thus obtained revealed that C was 67.22, H was 6.94 and N was 12.06 as calculated values (%) and C was 66.97, H was 6.91 and N was 11.85 as found values (%).

Figure 5:
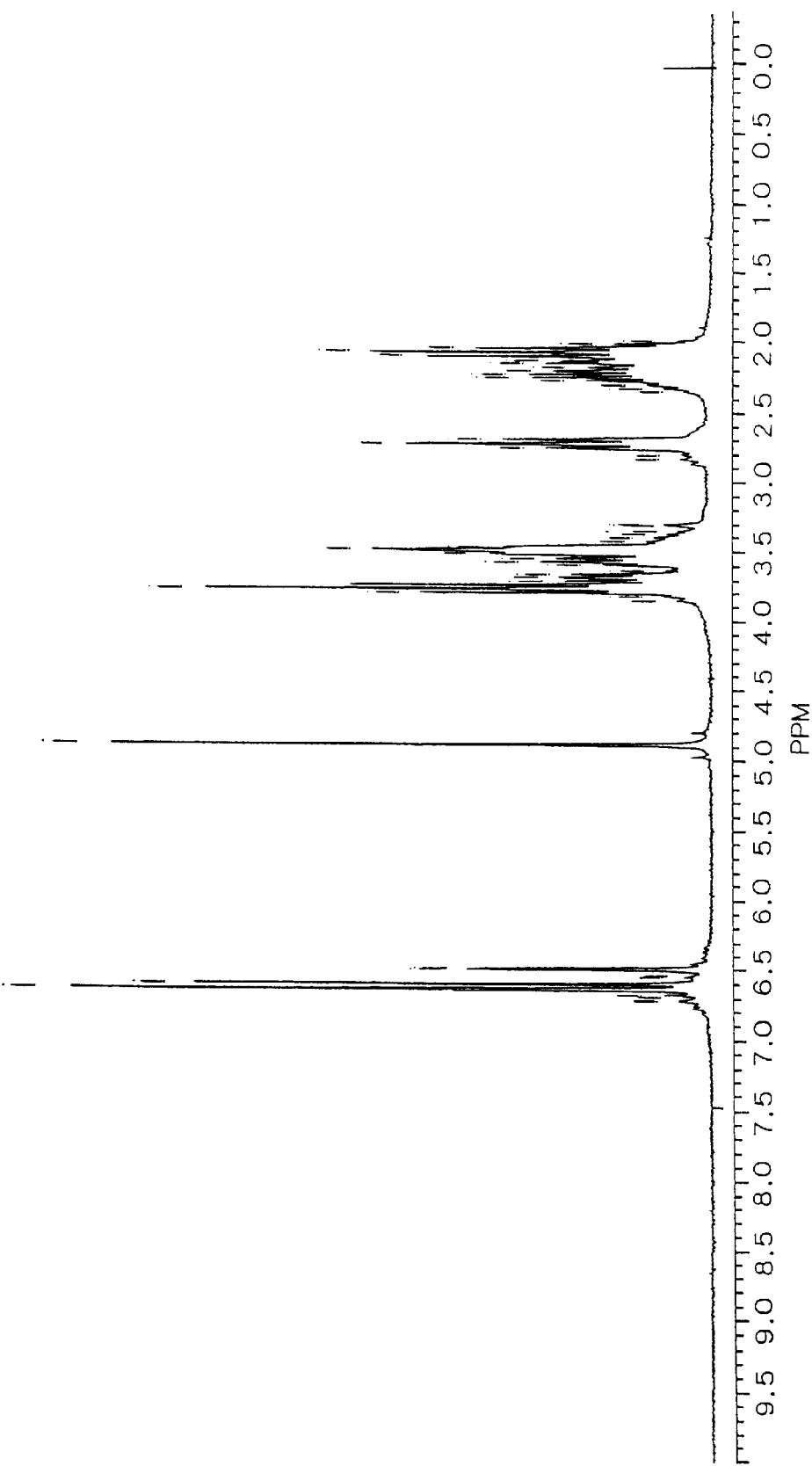
FIG. 5 shows a $^1$H-NMR spectrum of an addition product 3 obtained in Synthesis Example 3.
Figure 6:
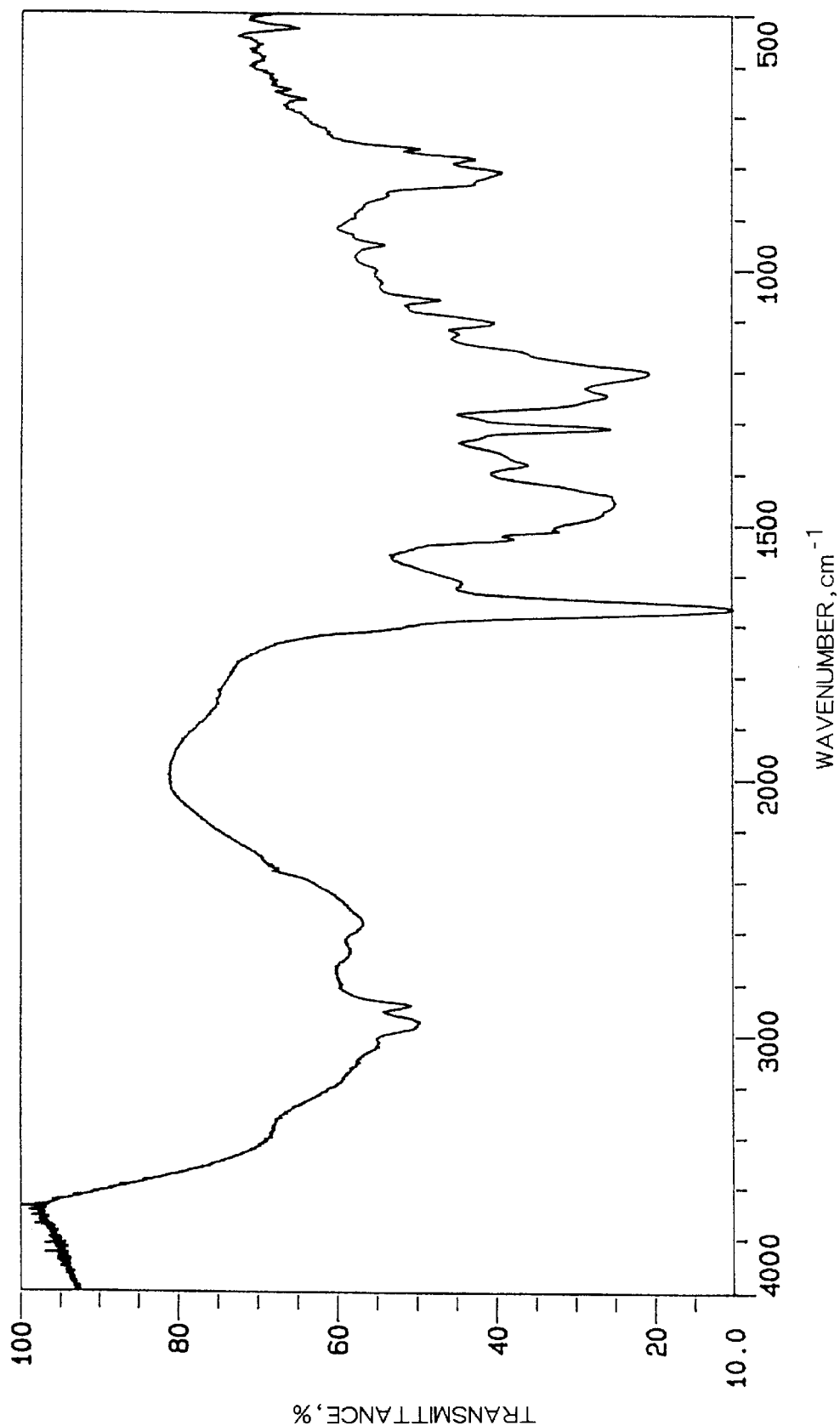
FIG. 6 shows an IR spectrum of the addition product 3 obtained in Synthesis Example 3.

From these results of elementary analysis, a $^1$H-NMR spectrum (measuring solvent: methanol-$d_4$) shown in FIG. 5 and an IR spectrum (KBr method) shown in FIG. 6, it was ascertained that a nitrogen-containing compound represented by the following structural formula (XVI) (herein "addition product 3") was obtained by the addition of the amidine compound with the quinone compound according to the present invention.

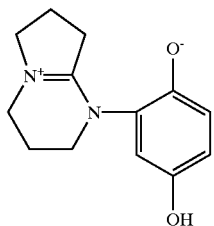

(XVI)

Synthesis Example 4

Synthesis of Curing Agent Resin Having Nitrogen-containing Compound Dissolved Therein:

Into a 3-litter four-necked flask having a thermometer, a stirrer and a dropping funnel, a phenol aralkyl resin MILEX (XL-225, available from Mitsui Chemicals Inc.; 450 parts) having hydroxyl group equivalent weight of 176 and having a softening point of 70° C. and 1,4-benzoquinone (21.9 parts) were put, and were dissolved under heating at 130° C. Thereafter, 1,8-diazabicyclo[5.4.0]undecene-7 (28.1 parts) was added dropwise with stirring. After further stirring for 3 hours, the reaction mixture was taken into a vat made of Teflon, and was left to cool to obtain a curing agent resin having the nitrogen-containing compound of the above formula (XI) dissolved therein.

Synthesis Example 5

Figure 7:
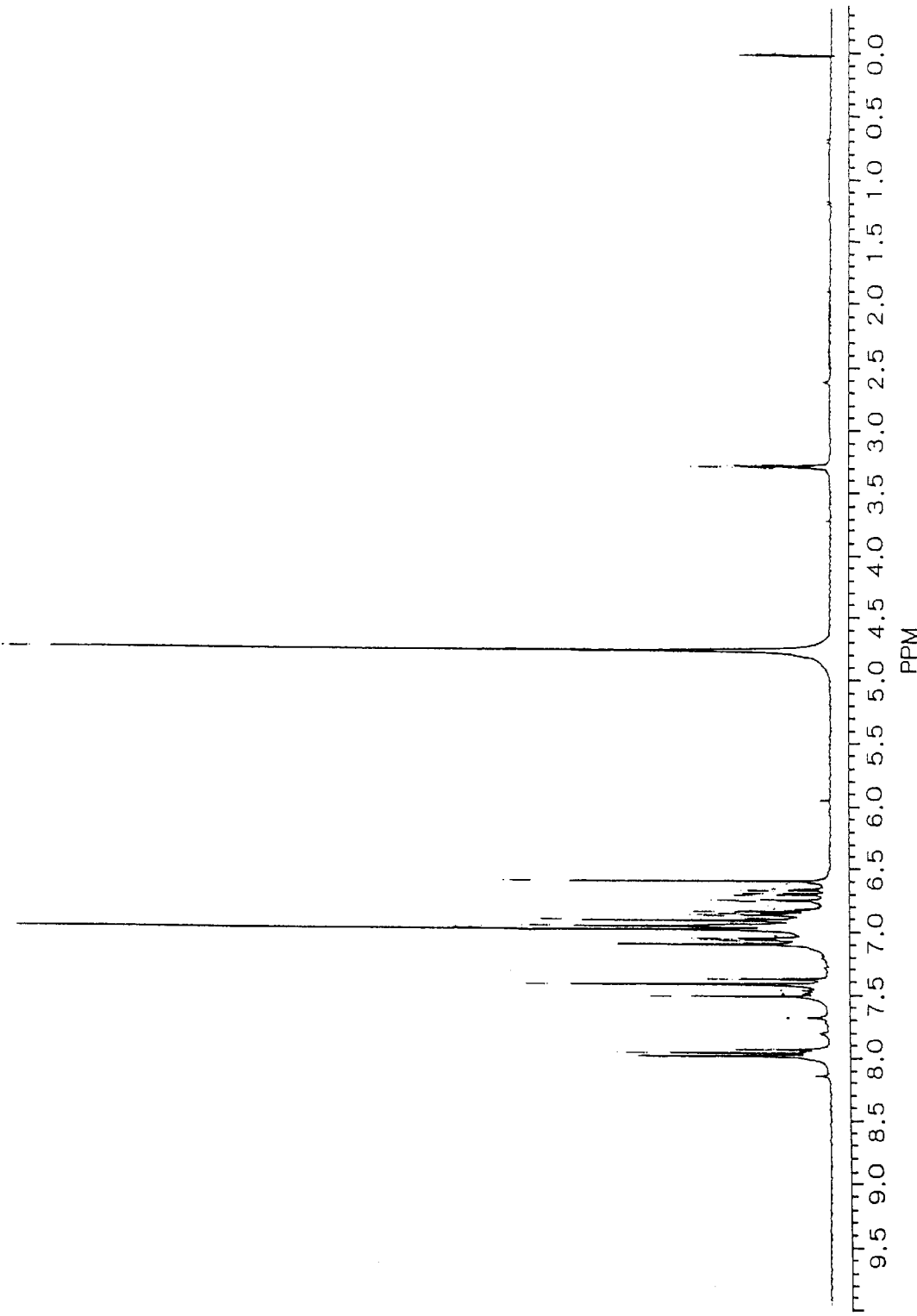
FIG. 7 shows a $^1$H-NMR spectrum of an addition product 4 obtained in Synthesis Example 5.

Synthesis of Addition Product 4:

Into a 1-litter four-necked flask having a thermometer, a stirrer and a dropping funnel, methyl isobutyl ketone (400 ml) and 1,4-benzoquinone (40.0 g) were put. These were stirred to dissolve the benzoquinone, and thereafter imidazole (12.6 g) dissolved in 200 ml of methyl isobutyl ketone was added dropwise over a period of 40 minutes while cooling and stirring the solution appropriately so as not to have a temperature higher than 40 degrees. After its addition had been completed, the reaction mixture was further stirred for 12 hours at room temperature. Thereafter, the reaction mixture was left for 4 days. Subsequently, the solid formed was collected by filtration by suction, followed by washing with methyl isobutyl ketone (400 ml) and then n-hexane (300 ml). The resultant solid was dried under reduced pressure to obtain a brown powder (29.6 g) nitrogen-containing compound (herein "addition product 4") formed by the addition of imidazole with 1,4-benzoquinone. Its $^1$H-NMR spectrum (measuring solvent: methanol-$d_4$/dimethyl sulfoxide-$d_6$) is shown in FIG. 7. The addition product 4 thus obtained is presumed to be a compound represented by the following formula (XXVI).

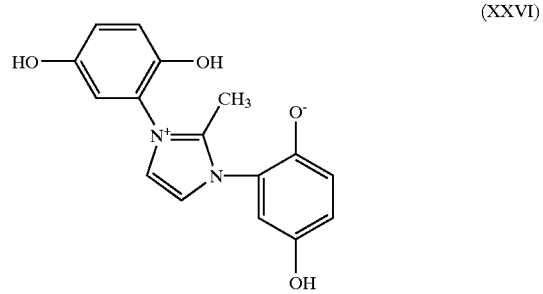

(XXVI)

Synthesis Example 6

Figure 8:
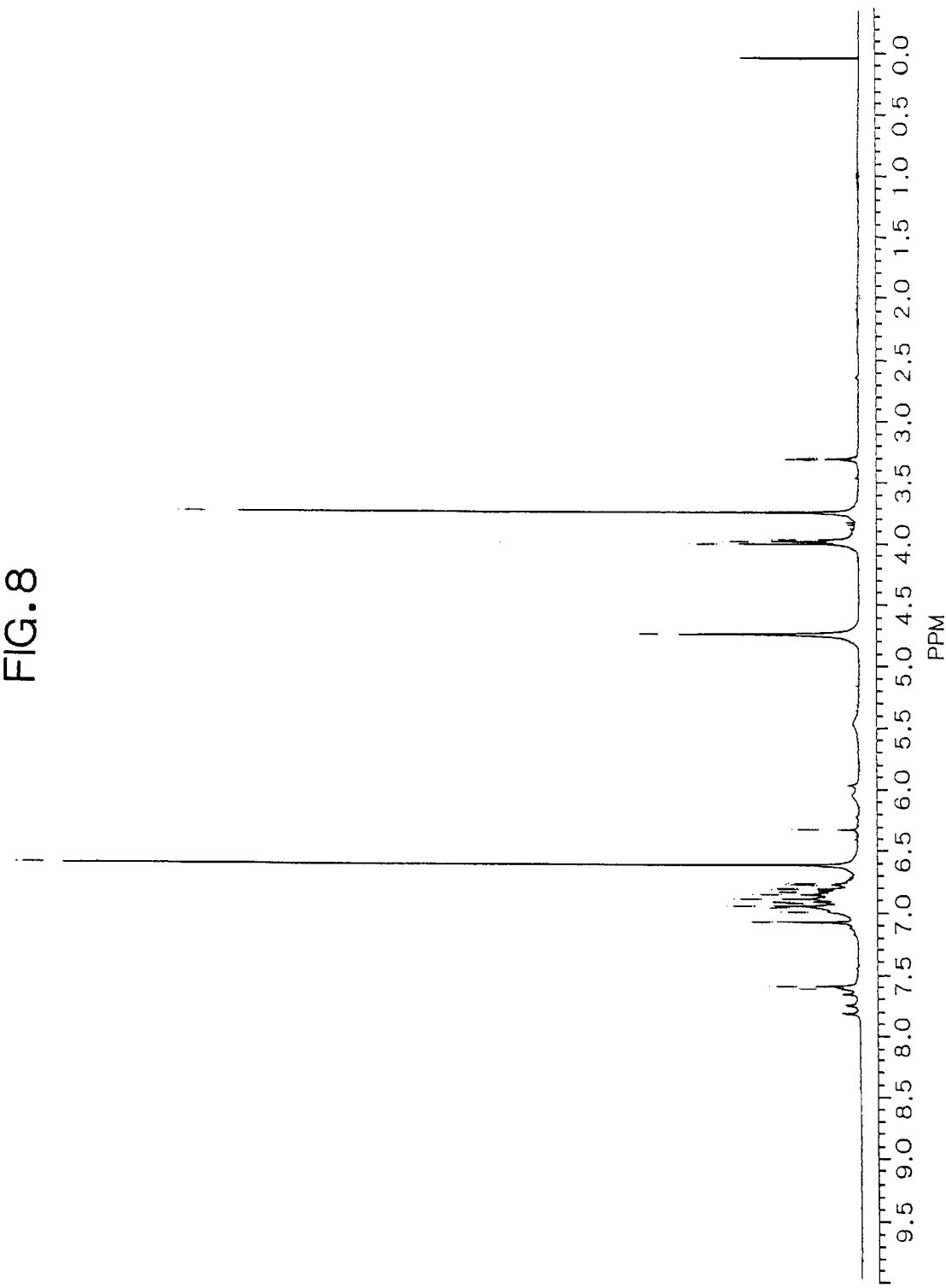
FIG. 8 shows a $^1$H-NMR spectrum of an addition product 5 obtained in Synthesis Example 6.

Synthesis of Addition Product 5:

Into a 500-ml four-necked flask having a thermometer, a stirrer and a dropping funnel, methyl isobutyl ketone (300 ml) and 1,4-benzoquinone (30.0 g) were put. These were stirred to dissolve the benzoquinone, and thereafter 1-methylimidazole (22.8 g) was added dropwise over a period of 40 minutes while cooling and stirring the solution appropriately so as not to have a temperature higher than 40 degrees. After its addition was completed, the reaction mixture was further stirred for 12 hours at room temperature. Thereafter, it was left for 4 days. Subsequently, the solid formed was collected by filtration by suction, followed by washing with methyl isobutyl ketone (400 ml) and then n-hexane (300 ml). The resultant solid was dried under reduced pressure to obtain a brown powder (30.7 g) nitrogen-containing compound (herein "addition product 5") formed by the addition of 1-methylimidazole with 1,4-benzoquinone. Its $^1$H-NMR spectrum (measuring solvent: methanol-$d_4$/dimethyl sulfoxide-$d_6$) is shown in FIG. 8. The addition product 5 thus obtained is presumed to be a compound represented by the following formula (XXVIII).

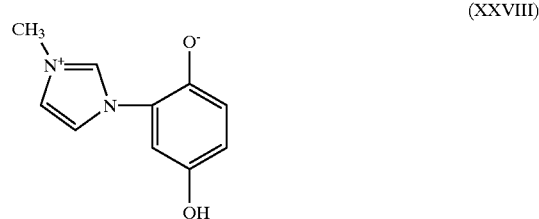

(XXVIII)

Synthesis Example 7

Figure 9:
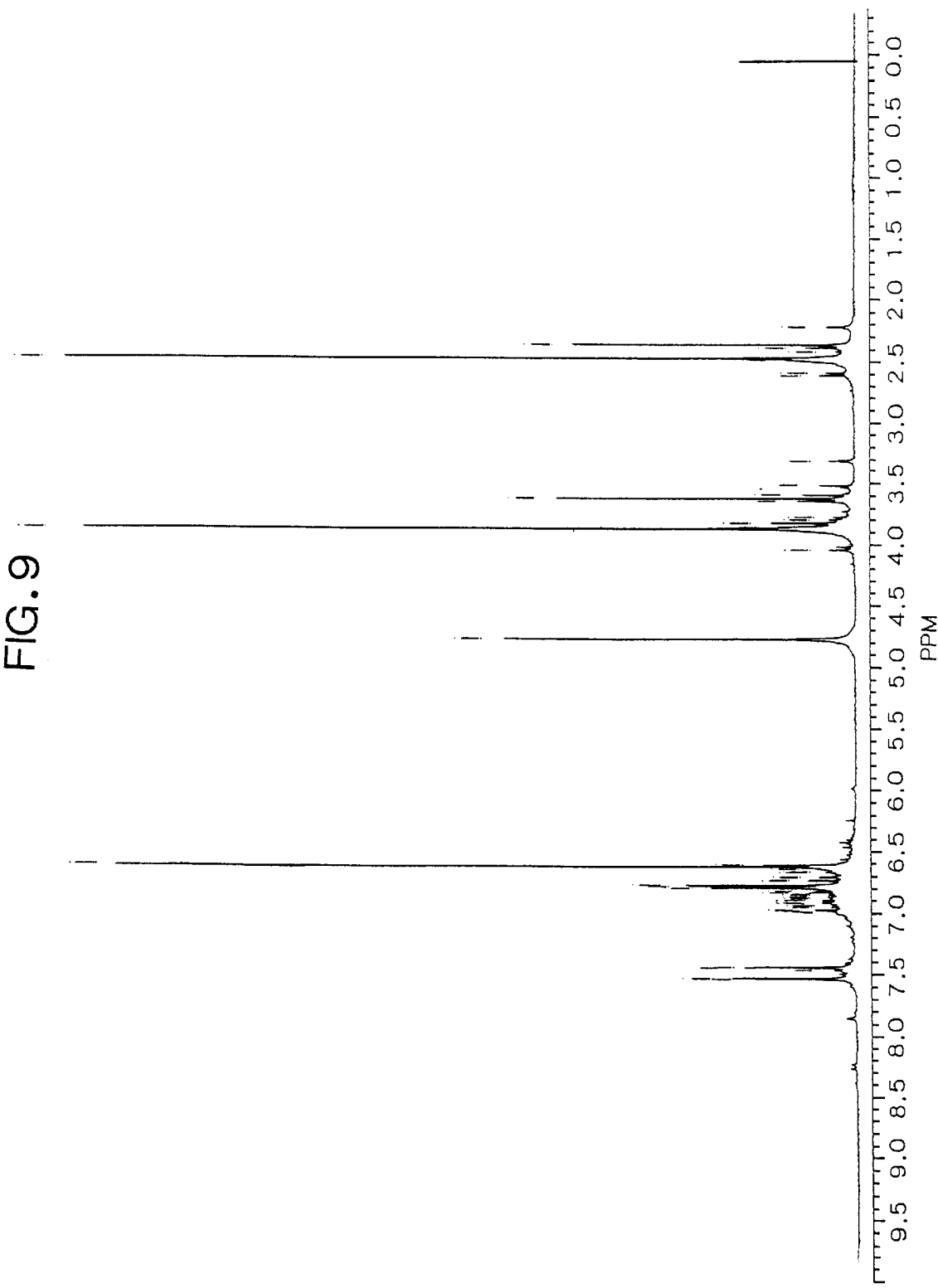
FIG. 9 shows a $^1$H-NMR spectrum of an addition product 6 obtained in Synthesis Example 7.

Synthesis of Addition Product 6:

Into a 500-ml four-necked flask having a thermometer, a stirrer and a dropping funnel, methyl isobutyl ketone (300 ml) and 1,4-benzoquinone (30.0 g) were put. These were stirred to dissolve the benzoquinone, and thereafter 1,2-dimethylimidazole (26.7 g) dissolved in 30 ml of methyl isobutyl ketone was added dropwise over a period of 40 minutes while cooling and stirring the solution appropriately so as not to have a temperature higher than 40 degrees. After its addition was completed, the reaction mixture was further stirred for 12 hours at room temperature. Thereafter, it was left for 4 days. Subsequently, the solid formed was collected by filtration by suction, followed by washing with methyl isobutyl ketone (400 ml) and then n-hexane (300 ml). The resultant solid was dried under reduced pressure to obtain a brown powder (36.2 g) nitrogen-containing compound (herein "addition product 6") formed by the addition of 1,2-dimethylimidazole with 1,4-benzoquinone. Its $^1$H-NMR spectrum (measuring solvent: methanol-$d_4$/dimethyl sulfoxide-$d_6$) is shown in FIG. 9. The addition product 6 thus obtained is presumed to be a compound represented by the following formula (XXV).

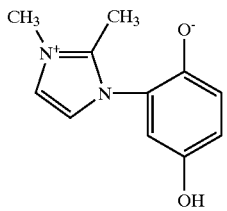

(XXV)

Synthesis Example 8

Figure 10:
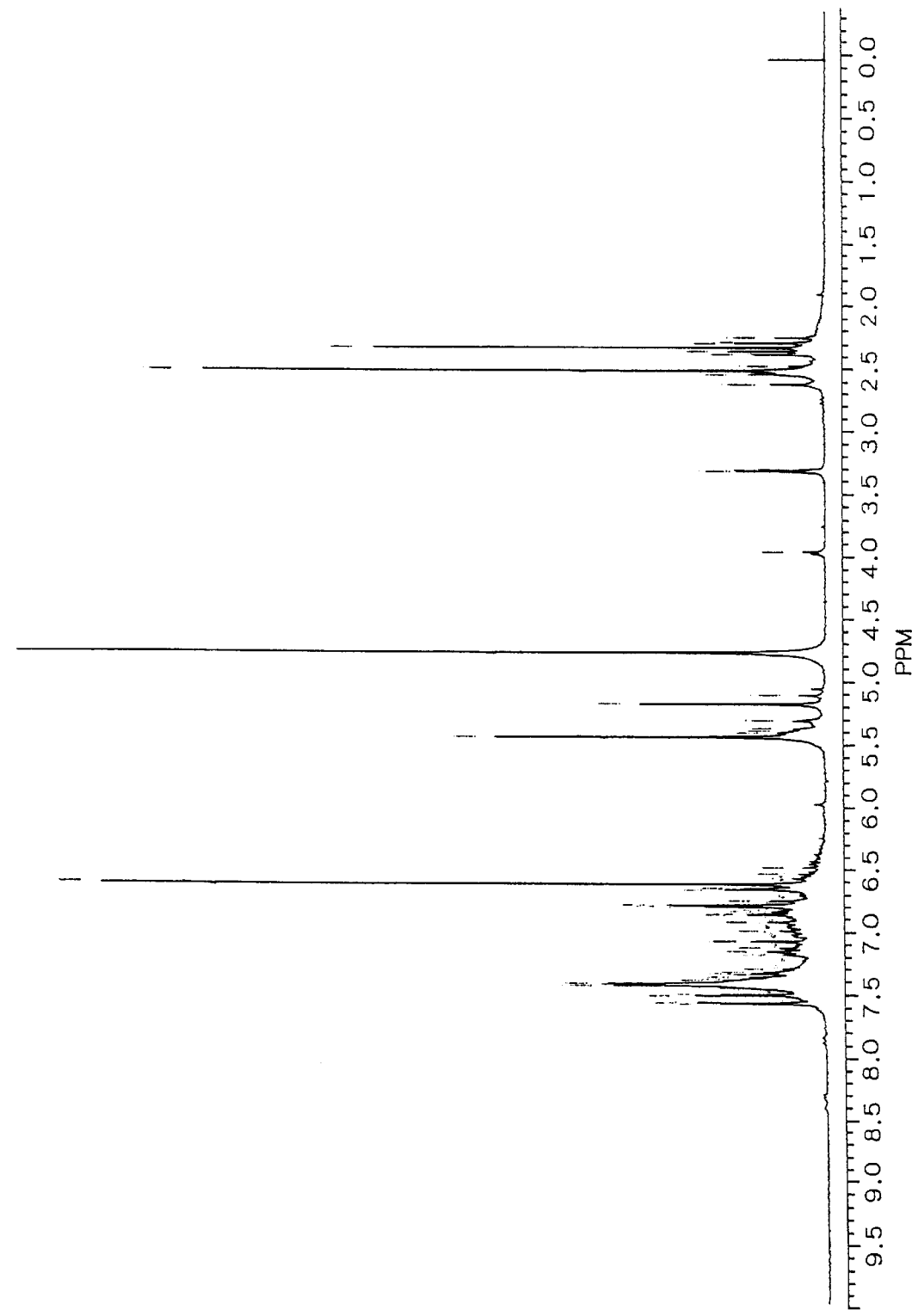
FIG. 10 shows a $^1$H-NMR spectrum of an addition product 7 obtained in Synthesis Example 8.

Synthesis of Addition Product 7:

Into a 500-ml four-necked flask having a thermometer, a stirrer and a dropping funnel, methyl isobutyl ketone (300 ml) and 1,4-benzoquinone (30.0 g) were put. These were stirred to dissolve the benzoquinone, and thereafter 1-benzyl-2-methylimidazole (47.8 g) dissolved in 100 ml of methyl isobutyl ketone was added dropwise over a period of 40 minutes while cooling and stirring the solution appropriately so as not to have a temperature higher than 40 degrees. After its addition was completed, the reaction mixture was further stirred for 12 hours at room temperature. Thereafter, it was left for 4 days. Subsequently, the solid formed was collected by filtration by suction, followed by washing with methyl isobutyl ketone (400 ml) and then n-hexane (300 ml). The resultant solid was dried under reduced pressure to obtain a brown powder (36.3 g) nitrogen-containing compound (herein "addition product 7") formed by the addition of 1-benzyl-2-methylimidazole with 1,4-benzoquinone. Its $^1$H-NMR spectrum (measuring solvent: methanol-$d_4$/dimethyl sulfoxide-$d_6$) is shown in FIG. 10. The addition product 7 thus obtained is presumed to be a compound represented by the following formula (XXIII).

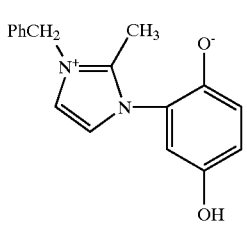

(XXIII)

Examples 1 to 10

The addition products 1 to 7 and curing agent resin obtained in Synthesis Examples 1 to 8 were used as curing accelerators. These were each mixed with an epoxy resin, a curing agent, an inorganic filler and other additive ingredients, and the mixture obtained was roll-kneaded under conditions of a kneading temperature of 80 to 90° C. and a kneading time of 10 minutes to obtain epoxy resin compositions of Examples 1 to 10.

The components mixed and amounts thereof in each Example are shown in Table 1. Units of numerical values shown in Table 1 are parts by weight unless particularly noted.

As the curing accelerators, in Examples 1 to 3 the addition product 1, obtained in Synthesis Example 1, was used; in Example 4 the addition product 2, obtained in Synthesis Example 2; in Example 5 the addition product 3, obtained in Synthesis Example 3; in Example 6 the curing agent resin having a nitrogen-containing compound dissolved therein, obtained in Synthesis Example 4; in Example 7 the addition product 4, obtained in Synthesis Example 5; in Example 8 the addition product 5, obtained in Synthesis Example 6; in Example 9 the addition product 6, obtained in Synthesis Example 7; and in Example 10 the addition product 7, obtained in Synthesis Example 8.

As the epoxy resin, used was a biphenyl skeleton type epoxy resin having an epoxy equivalent weight of 196 and a melting point of 106° C. (YX-4000H, available from YUKA SHELL EPOXY KABUSIKI KAISYA), a diphenylmethane skeleton type epoxy resin having an epoxy equivalent weight of 192 and a softening point of 79° C. (ESLV-80XY, available from Nippon Steel Chemical Co., Ltd.), a cresol novolak resin having an epoxy equivalent weight of 195 and a softening point of 67° C. (ESCN195, available from Sumitomo Chemical Co., Ltd.), or a brominated bisphenol-A epoxy resin having an epoxy equivalent weight of 393, a softening point of 67° C. and a bromine content of 48% by weight.

As the curing agent, a phenol-aralkyl resin MILEX (XL-225, available from Mitsui Chemicals Inc.), having a hydroxyl group equivalent weight of 176 and a softening point of 70° C., or a dicylclopentadiene skeleton type phenol novolak resin having a hydroxyl group equivalent weight of 167 and a softening point of 89° C. (DDP-L, available from Nippon Petrochemicals Co., Ltd.) was used. As the inorganic filler, fused quartz powder was used.

As the other additive ingredients, a coupling agent γ-glycidoxypropyltrimethoxysilane, carnauba wax, antimony trioxide and carbon black were used.

TABLE 1

| Items | Examples | | | | | | | | | |
|---|---|---|---|---|---|---|---|---|---|---|
| | 1 | 2 | 3 | 4 | 5 | 6 | 7 | 8 | 9 | 10 |
| Epoxy resin: | | | | | | | | | | |
| YX-4000H | 85 | | | 85 | 85 | 85 | 85 | 85 | 85 | 85 |
| ESLV-80XY | | 85 | | | | | | | | |

TABLE 1-continued

| Items | Examples | | | | | | | | | |
|---|---|---|---|---|---|---|---|---|---|---|
| | 1 | 2 | 3 | 4 | 5 | 6 | 7 | 8 | 9 | 10 |
| ESCN-195 | | | 85 | | | | | | | |
| Brominated epoxy resin | 15 | 15 | 15 | 15 | 15 | 15 | 15 | 15 | 15 | 15 |
| Curing agent: | | | | | | | | | | |
| XL-225 | 83.0 | 84.6 | | 84.7 | 83.0 | 53.4 | 83.0 | 83.0 | 83.0 | 83.0 |
| DPP-L | | | 79.2 | | | | | | | |
| Curing accelerator: | 3.7 | 3.7 | 3.7 | 3.9 | 3.3 | 33.3 | 5.1 | 3.4 | 3.6 | 5.0 |
| Carnauba wax: | 1 | 1 | 1 | 1 | 1 | 1 | 1 | 1 | 1 | 1 |
| Antimony trioxide: | 6 | 6 | 6 | 6 | 6 | 6 | 6 | 6 | 6 | 6 |
| Carbon black: | 1.3 | 1.3 | 1.3 | 1.3 | 1.3 | 1.3 | 1.3 | 1.3 | 1.3 | 1.3 |
| Coupling agent: | 7.0 | 7.0 | 7.0 | 7.0 | 7.0 | 7.0 | 7 | 7 | 7 | 7 |
| Fused quartz: (% by volume) | 74 | 74 | 74 | 74 | 74 | 74 | 74 | 74 | 74 | 74 |

Comparative Examples 1 to 9

Epoxy resin compositions of Comparative Examples 1 to 6 were obtained in the same manner as in Examples except that, as the curing accelerators, a phenol novolak salt of 1,8-diazabicyclo[5.4.0]undecene-7 (U-CAT SA-841, available from Sun Apro K.K.) was used in Comparative Examples 1 and 4 to 9, tetraphenyl borate of 1,8-diazabicyclo[5.4.0]undecene-7 in Comparative Example 2 and a phosphorus compound represented by the following formula (XIX) in Comparative Example 3, and according to the mixing formulation as shown in Table 2. Units of numerical values shown in Table 2 are parts by weight unless particularly noted.

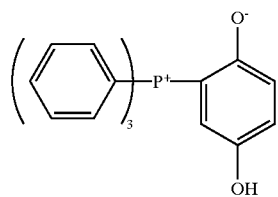

(XIX)

Measurement and Evaluation of Properties

Properties of the epoxy resin compositions produced in Examples and Comparative Examples were evaluated by test methods shown below.

(1) Hot Hardness:

Shore D Hardness of a Test Piece (diameter: 50 mm; thickness: 3 mm) molded under conditions of 180° C., 7 MPa and 90 seconds was measured.

(2) Hot Hardness After Moisture Absorption:

Hot hardness after storage for 72 hours under conditions of 25° C./50% RH was measured.

(3) Spiral Flow:

Flow distance (inch) when molded according to EEMI 1-66 under conditions of 180° C., 7 MPa and 90 seconds was measured.

(4) Storage Stability:

Results of spiral flow measured after the resin composition was stored at 25° C. for 72 hours or 144 hours were expressed in percentage with respect to spiral flow measured immediately after the composition was prepared.

The results of Examples 1 to 10 are shown in Table 3. As can be seen from the results, the resin compositions according to the present invention have a superior pot life of 90%

TABLE 2

| Items | Comparative Example | | | | | | | | |
|---|---|---|---|---|---|---|---|---|---|
| | 1 | 2 | 3 | 4 | 5 | 6 | 7 | 8 | 9 |
| Epoxy resin: | | | | | | | | | |
| YX-4000H | 85 | 85 | 85 | | | 85 | 85 | 85 | 85 |
| ESLV-80XY | | | | 85 | | | | | |
| ESCN-195 | | | | | 85 | | | | |
| Brominated epoxy resin | 15 | 15 | 15 | 15 | 15 | 15 | 15 | 15 | 15 |
| Curing agent: | | | | | | | | | |
| XL-225 | 72.9 | 83.0 | 83.0 | 74.1 | | 83 | 83 | 83 | 83 |
| DPP-L | | | | | 69.2 | | | | |
| Curing accelerator: | 9 | 9 | 3.4 | 9 | 9 | 1.2 | 1.5 | 1.7 | 3.1 |
| Carnauba wax: | 1 | 1 | 1 | 1 | 1 | 1 | 1 | 1 | 1 |
| Antimony trioxide: | 6 | 6 | 6 | 6 | 6 | 6 | 6 | 6 | 6 |
| Carbon black: | 1.3 | 1.3 | 1.3 | 1.3 | 1.3 | 1.3 | 1.3 | 1.3 | 1.3 |
| Coupling agent: | 6.7 | 7.2 | 7.0 | 6.8 | 6.7 | 7.0 | 7 | 7 | 7 |
| Fused quartz: (% by volume) | 74 | 74 | 74 | 74 | 74 | 74 | 74 | 74 | 74 | or more as storage stability at 25° C. for 72 hours, and also a good curability showing a hot hardness of 80 or more. They further showed a good hot hardness after moisture absorption, of 70 or more and at the same time a superior flow of 50 inches or more.

TABLE 3

| Items | Examples | | | | | | | | | |
|---|---|---|---|---|---|---|---|---|---|---|
| | 1 | 2 | 3 | 4 | 5 | 6 | 7 | 8 | 9 | 10 |
| Hot hardness: | 81 | 81 | 83 | 80 | 82 | 81 | 82 | 81 | 82 | 80 |
| Hot hardness after moisture absorption: | 72 | 74 | 78 | 72 | 79 | 73 | 80 | 79 | 81 | 79 |
| Spiral flow: (inch) | 64 | 65 | 53 | 66 | 62 | 61 | 58 | 57 | 51 | 57 |
| Storage stability: (%) | | | | | | | | | | |
| 72 hours | 90 | 90 | 99 | 92 | 90 | 90 | 91 | 90 | 92 | 90 |
| 144 hours | 79 | 80 | 97 | 81 | 78 | 81 | 83 | 82 | 83 | 82 |

In contrast thereto, in Comparative Examples, not containing any nitrogen-containing compound of the present invention, compositions of Comparative Examples 1, 4 and 5 were inferior in respect of flow properties and hot hardness after moisture absorption, and those of Comparative Examples 6 to 9 in respect of flow properties and pot life. The composition of Comparative Example 2 had too poor flow properties to be moldable. That of Comparative Example 3 had a poor curability after moisture absorption and a poor pot life. The results of evaluation in each Comparative Example are shown in Table 4.

TABLE 4

| Items | Comparative Example | | | | | | | | |
|---|---|---|---|---|---|---|---|---|---|
| | 1 | 2 | 3 | 4 | 5 | 6 | 7 | 8 | 9 |
| Hot hardness: | 79 | 0 | 79 | 79 | 82 | 82 | 81 | 82 | 80 |
| Hot hardness after moisture absorption: | 15 | 0 | 68 | 20 | 41 | 81 | 80 | 81 | 79 |
| Spiral flow: (inch) | 47 | >100 | 53 | 45 | 35 | 45 | 42 | 33 | 33 |
| Storage stability: (%) | | | | | | | | | |
| 72 hours | 93 | 99 | 70 | 94 | 99 | 70 | 73 | 72 | 70 |
| 144 hours | 82 | 99 | 53 | 80 | 97 | 52 | 56 | 54 | 53 |

POSSIBILITY OF INDUSTRIAL APPLICATION

As described above, the epoxy resin composition employing as a curing accelerator the nitrogen-containing compound obtained according to the present invention is superior in all the properties of rapid curability, curability after moisture absorption under moist condition, pot life and flow properties, and is preferably usable for the encapsulation of electronic component devices, in particular, semiconductors, promising a great industrial value.

What is claimed is:

1. A nitrogen-containing compound which is an addition product of an amidine compound represented by the following Formula (XXa):

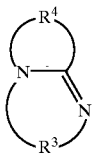

(XXa)

wherein $R^3$ and $R^4$ each represent a divalent organic group having 1 to 20 carbon atoms, with a quinone compound represented by the following Formula (II):

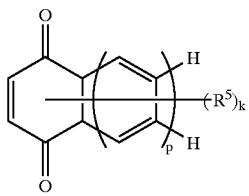

(II)

wherein $R^5$ represents a hydrogen atom or a monovalent organic group having 1 to 6 carbon atoms; and k and p represent an integer of 0 to 2 and an integer of 0 or 1, respectively.

2. The nitrogen-containing compound according to claim 1 wherein:

$R^3$ and $R^4$ are each selected from a substituted or unsubstituted, saturated or unsaturated hydrocarbon group, and a saturated or unsaturated hydrocarbon group containing a carbonyl linkage, an imino linkage or an ether linkage; and $R^5$ is selected from a hydrogen atom and an alkyl group, an alkoxyl group, an aryl group and an aralkyl group which have 1 to 6 carbon atoms.

3. The nitrogen-containing compound according to claim 2, wherein said quinone compound is 1,4-benzoquinone and/or 2,5-toluquinone.

4. The nitrogen-containing compound according to claim 2, wherein said amidine compound is a compound represented by the following Formula (I):

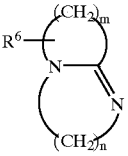

(I)

wherein $R^6$ is selected from a hydrogen atom and an alkyl group, a dialkyl-substituted amino group, an aryl group and an aralkyl group which have 1 to 12 carbon atoms; and m and n represent integers of 2 to 5 which are independent from each other.

5. The nitrogen-containing compound according to claim 4, wherein said amidine compound is 1,8-diazabicyclo[5.4.0]undecene-7 and/or 1,5-diazabicyclo[4.3.0]nonene-5.

6. A nitrogen-containing compound represented by the following Formula (XXIa):

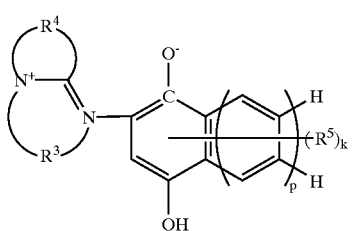

(XXIa)

wherein $R^3$ and $R^4$ each represent a divalent organic group having 1 to 20 carbon atoms; $R^5$ represents a hydrogen atom or a monovalent organic group having 1 to 6 carbon atoms; and k and p represent an integer of 0 to 2 and an integer of 0 or 1, respectively.

7. A resin curing accelerator comprising the nitrogen-containing compound according to claim 1.

8. A resin composition comprising a resin and a nitrogen-containing compound that is an addition product of an amidine compound represented by the following Formula (XXa) or (XXb),

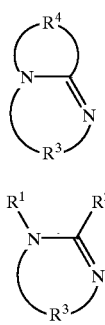

(XXa)

(XXb)

wherein $R^1$ and $R^2$ each represent a hydrogen atom, an amino group or a monovalent organic group having 1 to 20 carbon atoms; and $R^3$ and $R^4$ each represent a divalent organic group having 1 to 20 carbon atoms, with a quinone compound represented by the following Formula (II):

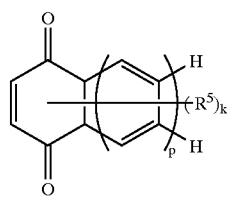

(II)

wherein $R^5$ represents a hydrogen atom or a monovalent organic group having 1 to 6 carbon atoms; and k and p represent an integer of 0 to 2 and an integer of 0 or 1, respectively.

9. An epoxy resin composition, which comprises as essential components;

(A) a nitrogen-containing compound that is an addition product of an amidine compound represented by the following Formula (XXa) or (XXb),

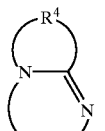

(XXa)

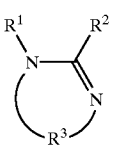

(XXb)

wherein $R^1$ and $R^2$ each represent a hydrogen atom, an amino group or a monovalent organic group having 1 to 20 carbon atoms; and $R^3$ and $R^4$ each represent a divalent organic group having 1 to 20 carbon atoms, with a quinone compound represented by the following Formula (II)

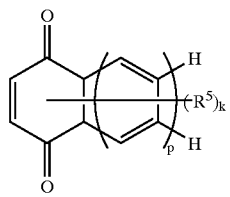

(II)

wherein $R^5$ represents a hydrogen atom or a monovalent organic group having 1 to 6 carbon atoms; and k and p represent an integer of 0 to 2 and an integer of 0 or 1, respectively;

(B) an epoxy resin having at least two epoxy groups in one molecule; and (C) a phenolic resin having at least two phenolic hydroxyl groups in one molecule.

10. The epoxy resin composition according to claim 9, which further comprises (D) an inorganic filler in an amount of at least 55% by volume based on the total weight of the composition.

11. The epoxy resin composition according to claim 9, wherein the equivalent weight ratio of the phenolic hydroxyl groups of the (C) phenolic resin to the epoxy groups of the (B) epoxy resin is from 0.5 to 2.

12. The epoxy resin composition according to claim 9, wherein said (B) epoxy resin contains at least one of epoxy resins represented by the following Formula (III) or (IV):

(III)

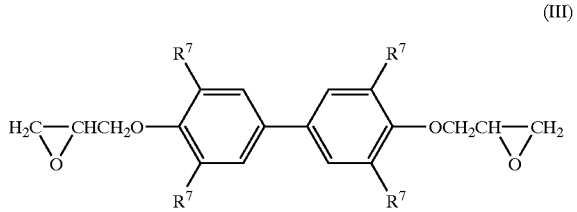

(IV)

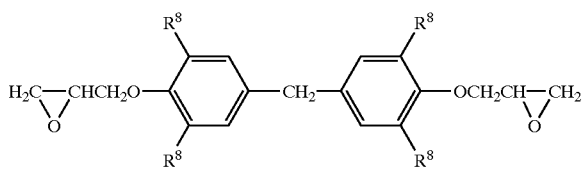

wherein $R^7$ and $R^8$ each represent a hydrogen atom or a methyl group.

13. The epoxy resin composition according to claim 9, wherein said (C) phenolic resin contains at least one of phenolic resins represented by the following Formula (V) or (VI):

(V)

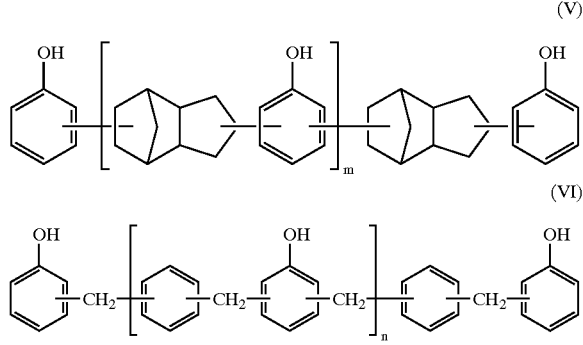

wherein m and n each represent 0 to 10.

14. An electronic component device having a device component encapsulated with the epoxy resin composition according to claim 9.

15. The epoxy resin composition according to claim 12, wherein said (C) phenolic resin contains at least one phenolic resin represented by the following Formula (V) or (VI):

(V)

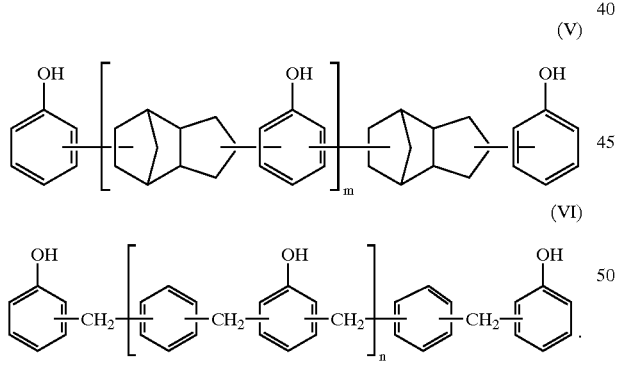

16. The epoxy resin composition of claim 9 wherein, in said (A) nitrogen-containing compound:
the $R^1$ and $R^2$ are each selected from a hydrogen atom and substituted or unsubstituted alkyl, aryl, aralkyl, alkenyl and alkoxyl groups;
$R^3$ and $R^4$ are each selected from a substituted or unsubstituted, saturated or unsaturated hydrocarbon group, and a saturated or unsaturated hydrocarbon group containing a carbonyl linkage, an imino linkage or an ether linkage; and
$R^5$ is selected from a hydrogen atom and an alkyl group, an alkoxyl group, an aryl group and an aralkyl group which have 1 to 6 carbon atoms.

17. The epoxy resin composition of claim 9 wherein, in said (A) nitrogen-containing compound, said quinone compound is 1,4-benzoquinone and/or 2,5-toluquinone.

18. The epoxy resin composition of claim 9 wherein, in said (A) nitrogen-containing compound, said amidine compound is a compound represented by the following Formula (I):

(I)

wherein $R^6$ is selected from a hydrogen atom and an alkyl group, a dialkyl-substituted amino group, an aryl group and an aralkyl group which have 1 to 12 carbon atoms; and m and n represent integers of 2 to 5 which are independent from each other.

19. The epoxy resin composition of claim 9 wherein, in said (A) nitrogen-containing compound said amidine compound is 1,8-diazabicyclo[5.4.0]undecene-7 and/or 1,5-diazabicyclo[4.3.0]nonene-5.

20. The epoxy resin composition of claim 9 wherein said (A) nitrogen-containing compound is represented by the following Formula (XXIa) or (XXIb):

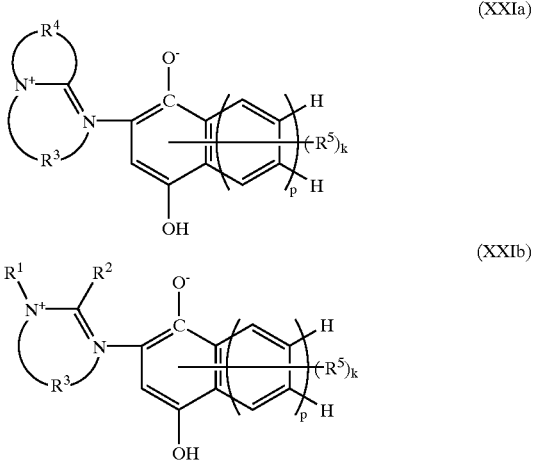

wherein $R^1$ and $R^2$ each represent a hydrogen atom or a monovalent organic group having 1 to 20 carbon atoms; $R^3$ and $R^4$ each represent a divalent organic group having 1 to 20 carbon atoms; $R^5$ represents a hydrogen atom or a monovalent organic group having 1 to 6 carbon atoms; and k and p represent an integer of 0 to 2 and an integer of 0 or 1, respectively.

21. A nitrogen-containing compound which is an addition product of an amidine compound represented by the following Formula (XXb),

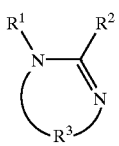

(XXb)

wherein $R^1$ and $R^2$ each represent a hydrogen atom, an amino group or a monovalent organic group having 1 to 20 carbon atoms; and $R^3$ is selected from a substituted or unsubstituted, saturated hydrocarbon group, and a saturated or unsaturated hydrocarbon group containing a carbonyl linkage, an imino linkage or an ether linkage, with a quinone compound represented by the following Formula (II):

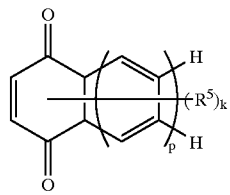

(II)

wherein $R^5$ represents a hydrogen atom or a monovalent organic group having 1 to 6 carbon atoms; and k and p represent an integer of 0 to 2 and an integer of 0 or 1, respectively.

22. The nitrogen-containing compound of claim 21 wherein:

$R^1$ and $R^2$ are each selected from a hydrogen atom and substituted or unsubstituted alkyl, aryl, aralkyl, alkenyl and alkoxyl groups; and $R^5$ is selected from a hydrogen atom and an alkyl group, an alkoxyl group, an aryl group and an aralkyl group which have 1 to 6 carbon atoms.

23. The nitrogen-containing compound of claim 21, wherein said quinone compound is 1,4-benzoquinone and/or 2,5-toluquinone.

24. A nitrogen-containing compound represented by the following Formula (XXIb):

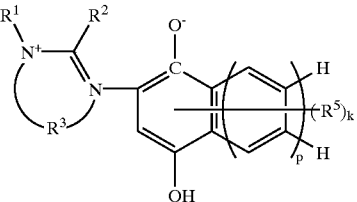

(XXIb)

wherein $R^1$ and $R^2$ each represent a hydrogen atom or a monovalent organic group having 1 to 20 carbon atoms; $R^3$ is selected from a substituted or unsubstituted, saturated hydrocarbon group, and a saturated or unsaturated hydrocarbon group containing a carbonyl linkage, an imino linkage or an ether linkage; $R^5$ represents a hydrogen atom or a monovalent organic group having 1 to 6 carbon atoms; and k and p represent an integer of 0 to 2 and an integer of 0 or 1, respectively.

\* \* \* \* \*